United States Patent
Verpoort et al.

(10) Patent No.: US 10,159,966 B2
(45) Date of Patent: Dec. 25, 2018

(54) CATALYST COMPLEXES WITH CARBENE LIGAND AND METHOD FOR MAKING SAME AND USE IN METATHESIS REACTION

(71) Applicant: GUANG MING INNOVATION COMPANY (WUHAN), Wuhan, Hubei (CN)

(72) Inventors: Francis W. C. Verpoort, Hubei (CN); Baoyi Yu, Hubei (CN)

(73) Assignee: GUANG MING INNOVATION COMPANY (WUHAN), Wuhan (CN)

( * ) Notice: Subject to any disclaimer, the term of this patent is extended or adjusted under 35 U.S.C. 154(b) by 544 days.

(21) Appl. No.: 14/759,091

(22) PCT Filed: Jan. 8, 2014

(86) PCT No.: PCT/CN2014/070318
§ 371 (c)(1),
(2) Date: Jul. 2, 2015

(87) PCT Pub. No.: WO2014/108071
PCT Pub. Date: Jul. 17, 2014

(65) Prior Publication Data
US 2015/0367338 A1    Dec. 24, 2015

(30) Foreign Application Priority Data

Jan. 10, 2013 (CN) .......................... 2013 1 0009234
Dec. 26, 2013 (CN) .......................... 2013 1 0737098

(51) Int. Cl.
| | | |
|---|---|---|
| *B01J 31/22* | (2006.01) | |
| *B01J 31/24* | (2006.01) | |
| *C07F 15/00* | (2006.01) | |
| *C08F 4/72* | (2006.01) | |
| *C08G 61/08* | (2006.01) | |

(52) U.S. Cl.
CPC ....... *B01J 31/2278* (2013.01); *B01J 31/2265* (2013.01); *B01J 31/2273* (2013.01); *B01J 31/2404* (2013.01); *C07F 15/0046* (2013.01); *C08F 4/72* (2013.01); *B01J 2231/543* (2013.01); *B01J 2531/821* (2013.01); *B01J 2531/825* (2013.01)

(58) Field of Classification Search
CPC .............. B01J 31/2265; B01J 2531/821; B01J 2531/825; C07F 15/0046; C07F 15/002
USPC .......................................... 548/103
See application file for complete search history.

(56) References Cited

U.S. PATENT DOCUMENTS

| | | | |
|---|---|---|---|
| 2008/0221345 A1* | 9/2008 | Winde | ................. B01J 31/2265 556/13 |
| 2011/0112349 A1* | 5/2011 | Holtcamp | ............ C07D 207/06 585/639 |

FOREIGN PATENT DOCUMENTS

| | | |
|---|---|---|
| CN | 101371991 A | 2/2009 |
| WO | 2011117571 A1 | 9/2011 |

OTHER PUBLICATIONS

International Search Report issued by the State Intellectual Property Office of the P.R. China dated Apr. 22, 2014 for Application No. PCT/CN2014/070318.

Poater, Albert et al., "Comparison of different ruthenium-alkylidene bonds in the activation step with N-heterocyclic carbene Ru-catalysts for olefins metathesis", Dalton Trans Nov. 9, 2011;40(42)11066-9.

* cited by examiner

*Primary Examiner* — Fred M Teskin
(74) *Attorney, Agent, or Firm* — Locke Lord LLP; Tim Tingkang Xia, Esq.

(57) ABSTRACT

This invention relates to catalyst compounds and the synthesis and applications useful in olefin metathesis reactions. The catalyst compounds of the invention are represented by the formula (I): wherein M is a Group 8 metal; $X^1$ and $X^2$ are anionic ligands; $L^1$ and $L^2$ are neutral two electron donor ligands. The present invention also relates to an easy applicable catalyst synthesis and the application in different olefin metathesis processes, e.g. Reaction Injection Molding (RIM), process to make α-olefins from fatty acid ester, e.g. methyl oleate.

13 Claims, 2 Drawing Sheets

CATALYST COMPLEXES WITH CARBENE LIGAND AND METHOD FOR MAKING SAME AND USE IN METATHESIS REACTION

FIELD OF THE INVENTION

This invention relates to olefin metathesis, more particularly, metathesis catalyst compounds, their synthesis and processes for the use thereof in metathesis reaction.

BACKGROUND OF THE INVENTION

Olefin metathesis is a catalytic process including, as a key step, a reaction between a first olefin and a first transition metal alkylidene complex, thus producing an unstable intermediate metallacyclobutane ring which then undergoes transformation into a second olefin and a second transition metal alkylidene complex according to equation (1) hereunder. Reactions of this kind are reversible and in competition with one another, so the overall result heavily depends on their respective rates and, when formation of volatile or insoluble products occur, displacement of equilibrium.

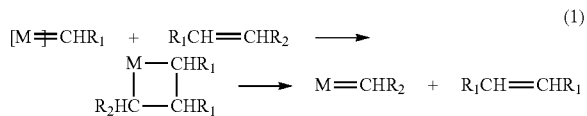

Metathesis reactions are extensively applied in the field of chemical reactions, e.g. Ring closing metathesis (RCM), Cross metathesis (CM), Ring opening metathesis (ROM), Ring opening metathesis polymerization (ROMP), acyclic diene metathesis (ADMET), self-metathesis, conversion of olefins with alkynes (enyne metathesis), polymerization of alkynes, and so on.

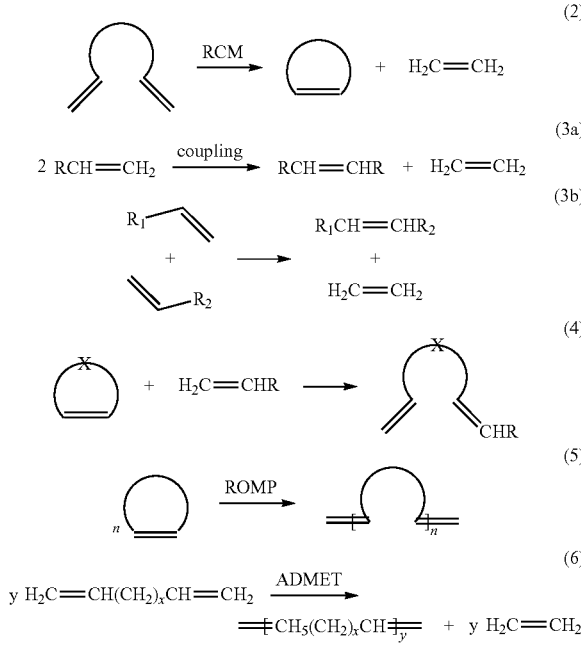

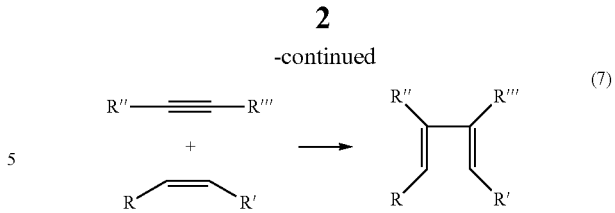

Typical applications of olefin metathesis but not limited are Reaction Injection Molding (RIM) of dicyclopentadiene (DCPD), which is an example of the ring opening metathesis polymerization; ROMP of norbornene derivates; ethenolysis, a chemical process in which internal olefins are degraded using ethylene as the reagent. The reaction is an example of cross metathesis; CM of ethene with 2-butene; depolymerization of unsaturated polymers.

Of potentially greater interest than homo-coupling (equation 3a) is cross-coupling between two different terminal olefins (equation 3b). Coupling reactions involving dienes lead to linear and cyclic dimers, oligomers, and, ultimately, linear or cyclic polymers (equation 6). In general, the latter reaction is favoured in highly concentrated solutions or in bulk, while cyclisation is favoured at low concentrations. When intra-molecular coupling of a diene occurs so as to produce a cyclic alkene, the process is called ring-closing metathesis (equation 2). Cyclic olefins can be opened and oligomerised or polymerised (ring opening metathesis polymerisation shown in equation 5). When the alkylidene catalyst reacts more rapidly with the cyclic olefin (e.g. a norbornene or a cyclobutene) than with a carbon-carbon double bond in the growing polymer chain, then a "living ring opening metathesis polymerisation" may result, i.e. there is little termination during or after the polymerization reaction. Strained rings may be opened using an alkylidene catalyst with a second alkene following the mechanisms of the Cross Metathesis. The driving force is the relief of ring strain. As the products contain terminal vinyl groups, further reactions of the Cross Metathesis variety may occur. Therefore, the reaction conditions (time, concentrations, . . . ) must be optimized to favor the desired product (equation 4). The enyne metathesis is a metalcarbene-catalyzed bond reorganization reaction between alkynes and alkenes to produce 1,3-dienes. The intermolecular process is called Cross-Enyne Metathesis (7), whereas intramolecular reactions are referred as Ring-Closing Enyne Metathesis (RCEYM).

The cross-metathesis of two reactant olefins, where each reactant olefin comprises at least one unsaturation site, to produce new olefins, which are different from the reactant olefins, is of significant commercial importance. One or more catalytic metals, usually one or more transition metals, usually catalyze the cross-metathesis reaction.

One such commercially significant application is the cross-metathesis of ethylene and internal olefins to produce alpha-olefins, which is generally referred to as ethenolysis. More specific, the cross-metathesis of ethylene and an internal olefin to produce linear α-olefins is of particular commercial importance. Linear α-olefins are useful as monomers or co-monomers in certain (co)polymers poly α-olefins and/or as intermediates in the production of epoxides, amines, oxo alcohols, synthetic lubricants, synthetic fatty acids and alkylated aromatics. Olefins Conversion Technology™, based upon the Phillips Triolefin Process, is an example of an ethenolysis reaction converting ethylene and 2-butene into propylene. These processes apply heterogeneous catalysts based on tungsten and rheniumoxides, which have not proven effective for internal olefins containing functional groups such as cis-methyl oleate, a fatty acid methyl ester.

1-Decene is a co-product typically produced in the cross-metathesis of ethylene and methyl oleate. Alkyl oleates are fatty acid esters that can be major components in biodiesel produced by the transesterification of alcohol and vegetable oils. Vegetable oils containing at least one site of unsaturation include canola, soybean, palm, peanut, mustard, sunflower, tung, tall, perilla, grapeseed, rapeseed, linseed, safflower, pumpkin, corn and many other oils extracted from plant seeds. Alkyl erucates similarly are fatty acid esters that can be major components in biodiesel. Useful biodiesel compositions are those, which typically have high concentrations of oleate and erucate esters. These fatty acid esters preferably have one site of unsaturation such that cross-metathesis with ethylene yields 1-decene as a co-product.

Vegetables oils used in food preparation (fritting of meat, vegetables, . . . ) can be recuperated and after purification, be converted applying e.g. ethenolysis into useful products applicable in biodiesel.

Biodiesel is a fuel prepared from renewable sources, such as plant oils or animal fats. To produce biodiesel, triacylglycerides, the major compound in plant oils and animal fats, are converted to fatty acid alkyl esters (i.e., biodiesel) and glycerol via reaction with an alcohol in the presence of a base, acid, or enzyme catalyst. Biodiesel fuel can be used in diesel engines, either alone or in a blend with petroleum-based diesel, or can be further modified to produce other chemical products.

Several Metal-carbene complexes are known for olefin metathesis however the difference between those structures can be found in the carbene part. Patents WO-A-96/04289 and WO-A-97/06185 are examples of metathesis catalysts having the general structure

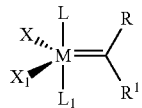

Where:

M is Os or Ru, R and $R^1$ organic parts from the carbene fragment which have a great structural variability, X and $X_1$ are anionic ligands and L and $L_1$ represents neutral electron donors. "anionic ligands" are, according the literature in the field of olefin metathesis catalysts, ligands which are negative charged and thus bearing a full electron shell when they are removed from the metal center A well-known example of this class of compounds is the Grubbs $1^{st}$ generation catalysts

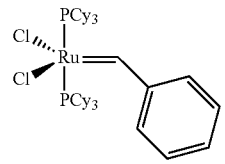

Another well-known example of this class of compounds is the Grubbs' $2^{nd}$ generation catalyst which is described in WO-A-0071554 and the hexa-coordinated "Grubbs $3^{rd}$ generation catalyst described in WO-A03/011455.

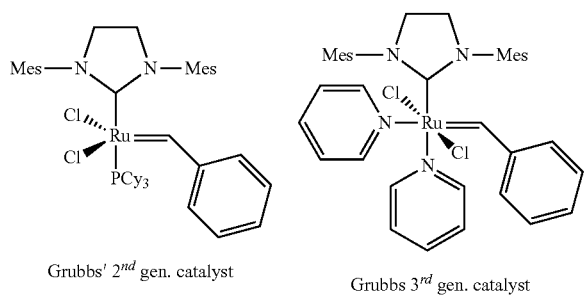

Grubbs' $2^{nd}$ gen. catalyst

Grubbs $3^{rd}$ gen. catalyst

There are still some other well-known catalysts described in literature which are very useful in the area of olefin metathesis, and which serve as background information for this application. These catalysts are described in US 2002/0107138 A1 and WO-A-2004/035596 and are respectively known as the "Hoveyda catalysts" and the "Grela catalyst"

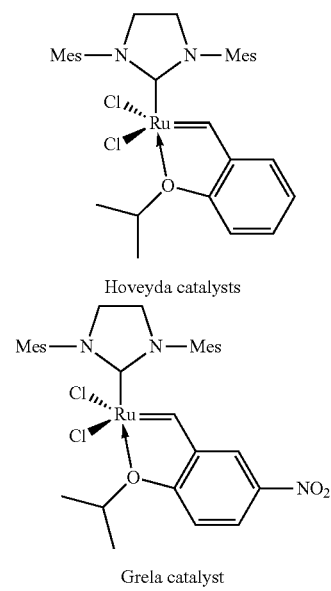

Hoveyda catalysts

Grela catalyst

Furthermore, other catalysts are known where both carbon atoms of the carbene fragment are bridged, a few of these representatives are given

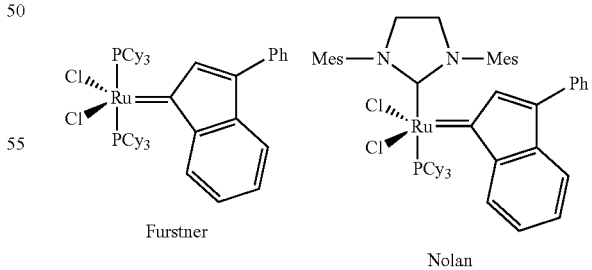

Furstner

Nolan

The bridged carbene fragment was firstly synthesized by Hill et al. (K. J. Harlow, A. F. Hill, J. D. E. T. Wilton-Ety, J. Chem. Soc. Dalton Trans. 1999, 285-291), however the structure was wrongly interpreted. Furstner et al. corrected this misinterpretation (J. Org. Chem. 1999, 64, 8275-8280) and a full characterization was described. It followed that reorganization takes place whereby the carbon atoms of the carbene fragment are bridged and generating in this specific case a "3-phenyl-indenylidene carbene" (Chem. Eur. J. 2001, 7, No 22, 4811-4820). Analogues of this catalyst bearing one NHC-ligand and one phosphine ligand where described by Nolan in WO-A-00/15339. These types of compounds are not only catalysts for the olefin metathesis; they also can be used as starting product to produce other ruthenium-carbene compounds via cross metathesis (WO-A-2004/112951).

Furthermore, in US-A-2003/0100776 on page 8, paragraph [0087] are catalysts described where the carbon atoms of the carbene part are bridged and whereby the newly formed cyclic group can be aliphatic or aromatic and can bear substituents or hetero atoms. Additionally, it is said that the generated ring structure is constructed of 4 to 12 and preferable 5 to 8 atoms contains. However, no explicit ring structures or examples are described or given.

In PCT/US2010/059703 (WO 2011/100022 A2) an indenylidene based catalyst is described whereby one phosphine ligand is substituted by an neutral donor ligand which is linked to the indenylidene carbene. The resulting catalyst is a 3-phenylindenylidene Hoveyda analogue catalyst.

In PCT/US2011/029690 (WO 2011/119778 A2) a hexa-coordinated catalyst is claimed, however in this document no catalysts were isolated, a synthetic method for the in-situ generation of olefin metathesis catalysts is disclosed since according to Schrödi the synthesis of these complexes is relatively cumbersome. The synthesis usually involves more than one step and requires isolation of the catalysts to remove catalyst-inhibiting byproducts such as liberated phosphines. The resulting in-situ generated catalysts are all phenylindenylidene Hoveyda analogue catalysts.

Other catalysts where the carbon atoms of the carbene part are bridged having the indenylidene basic structure are until now not know

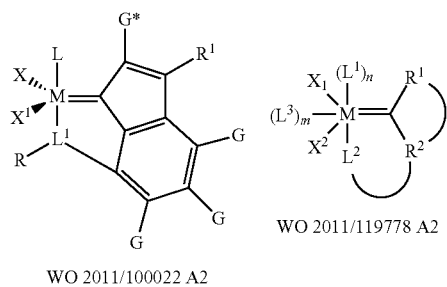

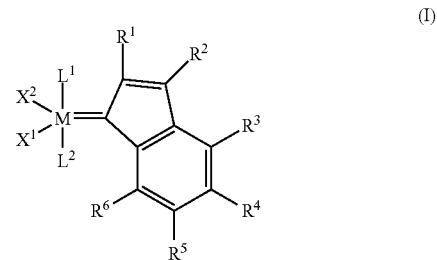

Despite the advances achieved in the preparation and development of olefin metathesis catalysts, a continuing need exists for new improved synthetic methods and new catalysts. Of particular interest are methods that provide the preparation of new catalysts, which easily can be prepared on industrial scale.

Furthermore, the instant invention's metathesis catalyst compounds provide both a mild and commercially economical and an "atom-economical" route to desirable olefins, which in turn may be useful in the preparation of linear alpha-olefins, unsaturated polymers, cyclic olefins, etc.

The synthesis of $RuCl_2(PCy_3)_2$(3-phenylindenylene) has proven useful in providing an easy route to ruthenium alkylidenes which avoids costly diazo preparations (Platinum Metals Rev. 2005, 49, 33).

In order to obtain an economically viable process for linear α-olefins (e.g. 1-decene) production via the cross-metathesis of ethylene and biodiesel (such as animal or vegetable oils), higher activity catalysts or more stable catalysts must be developed. Moreover, there is still a need for the development of catalysts with equivalent or better performance characteristics but synthesized directly from less expensive and readily available starting materials.

SUMMARY OF THE INVENTION

The present invention is directed to addressing one or more of the above-mentioned issues. The invention is based on the unexpected finding that improved olefin metathesis catalysts having a general structure of formula (I) can be obtained by modifying the alkylidene part of group 8 catalysts of the prior art. The present invention is also based on the unexpected finding that the synthesis time of the organometallic compounds of formula (I) can be reduced to one hour or less while maintaining high to excellent yields.

(I)

The organometallic catalyst compound of the present invention can be prepared by contacting a Group 8 metal precursor compound with an acetylenic compound which alternatively can bear a chelating moiety.

Wherein,

M is a Group 8 metal, preferably ruthenium or osmium, $R^1$-$R^6$ are identical or different and selected from hydrocarbyl, substituted hydrocarbyl, heteroatom containing hydrocarbyl, substituted heteroatom-containing hydrocarbyl, and functional groups wherein alternatively in each case two directly adjacent radicals from the group of $R^1$-$R^6$, including the ring carbon atoms to which they are attached by a cyclic bridging group, generating one or more cyclic structures, including aromatic structures wherein alternatively $R^6$ is optionally bridged with a different ligand of the metal carbene complex catalyst, $X^1$ and $X^2$ are identical or different and represent two ligands, preferably anionic ligands.

$L^1$ and $X^1$ may be joined to form a multidentate mono-anionic group and may form single ring of up to 30 non-hydrogen atoms or a multinuclear ring system of up to 30 non-hydrogen atoms;

$L^1$ and $L^2$ are identical or different ligands, preferably represent neutral electron donors, wherein $L^2$ can be bridged alternatively by a radical $R^6$.

In another aspect, the invention provides novel organometallic compounds according to the above structure.

In an extra aspect, the invention provides a method for performing a catalytic metathesis reaction comprising contacting at least one olefin or olefinic compound with the metathesis catalyst of the invention. An olefin includes a single olefin as well as a combination or mixture of two or more olefins, reference to "a substituent" encompasses a single substituent as well as two or more substituents, and the like.

In the context of this invention, all the above and below mentioned, general or preferred ranges of definitions, parameters or elucidations among one another, or also between the respective ranges and preferred ranges can be combined in any manner.

In the context of this invention, related to the different types of metathesis catalysts, the term "substituted" means that a hydrogen atom or an atom is replaced by a specified group or an atom, and the valence of the atom indicated is not exceeded and the substitution leads to a stable compound.

DETAILED DESCRIPTION

Terminology and Definitions

Figure 1:
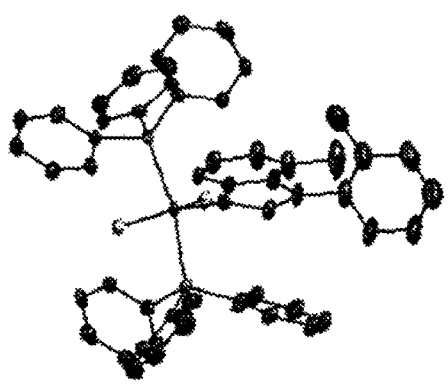
FIG. 1 is crystal structure of $(PPh_3)_2Cl_2Ru(3\text{-}2\text{-methylphenyl-5-methylinden-1-ylidene})$ (1 D).
Figure 2:
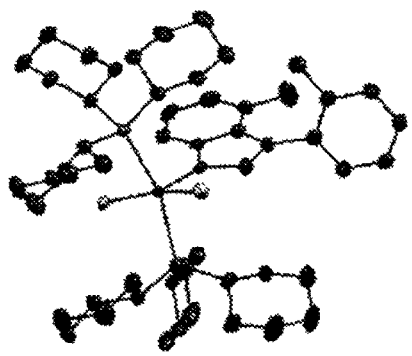
FIG. 2 is crystal structure of $(PCy_3)_2Cl_2Ru(3\text{-}2\text{-methylphenyl-5-methylinden-1-ylidene})$ (8).

Unless otherwise mentioned, the invention is not limited to specific reactants, substituents, catalysts, reaction conditions, or the like, as such may vary. It is also to be understood that the terminology used herein is for the purpose of describing particular embodiments only and is not intended to be limiting.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "$C_1$-$C_6$-alkyl" intends an alkyl group of 1 to 6 carbon atoms, and the specific term "cycloalkyl" intends a cyclic alkyl group, typically having 3 to 8 carbon atoms.

The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the term "alkyl" include linear, branched, cyclic, unsubstituted, substituted, and/or heteroatom-containing alkyl.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, and the like. Preferred alkenyl groups herein contain 2 to about 12 carbon atoms. The term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the term "alkenyl" include linear, branched, cyclic, unsubstituted, substituted, and/or heteroatom-containing alkenyl.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the term "alkynyl" include linear, branched, unsubstituted, substituted, and/or heteroatom-containing alkynyl respectively.

The term "alkoxy" as used herein intends an alkyl group bound through a single, terminal ether linkage; that is, an "alkoxy" group may be represented as —O-alkyl where alkyl is as defined above. Analogously, "alkenyloxy" refers to an alkenyl group bound through a single, terminal ether linkage, and "alkynyloxy" refers to an alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxyphenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms. Alkaryl groups include, but not limit to, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatomcontaining hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyalkyl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO), carbamoyl (CO)—$NH_2$), mono-($C_1$-$C_{24}$ alkyl) substituted carbamoyl (CO)—NH($C_1$-$C_{24}$ alkyl)), di-($C_1$-$C_{24}$ alkyl)-substituted carbamoyl (—(CO)N($C_1$-$C_{24}$ alkyl)$_2$), mono-($C_5$-$C_{24}$ aryl)-substituted carbamoyl (—(CO)—NH-aryl), di-($C_5$-$C_{24}$ aryl) substituted carbamoyl (CO)—N($C_5$-$C_{24}$ aryl)$_2$), N(($C_1$-$C_{24}$ alkyl) ($C_5$-$C_{24}$ aryl))-substituted carbamoyl, thiocarbamoyl (—(CS)—$NH_2$), mono-($C_1$-$C_{24}$ alkyl)-substituted thiocarbamoyl (—(CS)NH($C_1$-$C_{24}$ alkyl)), di-($C_1$-$C_{24}$ alkyl)-substituted thiocarbamoyl (CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl ((CS)—N($C_5$-$C_{24}$ aryl)$_2$), N—($C_1$-$C_{24}$ alkyl)N—($C_5$-$C_{24}$ aryl)-substituted thiocarbamoyl, carbamido (NH—(CO)—$NH_2$), cyano (—C≡N), cyanato (—O—C≡N), thiocyanato (—S—C≡N), formyl (—(CO)—H), thioformyl (—(CS)—H), amino (—$NH_2$), mono-($C_1$-$C_{24}$ alkyl)-substituted amino, di-($C_1$-$C_{24}$ alkyl) substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_5$-$C_{24}$ arylsulfonyl (—$SO_2$-aryl), boryl (—$BH_2$), borono (—B(OH)$_2$), boronato (—B(OR)$_2$ where R is alkyl or other hydrocarbyl), phosphono (—P(O)(OH)$_2$), phosphonato (—P(O)($O^-$)$_2$), phosphinato (—P(O)($O^-$)), phosphor (—$PO_2$), and phosphino (—$PH_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl", "functionalized alkyl", "functionalized olefin", "functionalized cyclic olefin", and the like, is meant that in the hydrocarbyl, alkyl, olefin, cyclic olefin, or other moiety, at least one hydrogen atom bound to a carbon (or other) atom is replaced with one or more functional groups such as those described hereinabove.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

The present invention comprises a novel family of metathesis catalyst compounds useful for the different types of olefin metathesis reactions, including but not limited to Ring closing metathesis (RCM), Cross metathesis (CM), Ring opening metathesis (ROM), Ring opening metathesis polymerization (ROMP), acyclic diene metathesis (AD-MET), self-metathesis, conversion of olefins with alkynes (enyne metathesis), polymerization of alkynes, ethylene cross-metathesis and so on

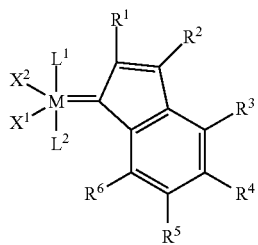

(I)

and wherein

M is a Group 8 metal, preferably ruthenium or osmium, $R^1$-$R^6$ are identical or different and represents hydrogen, halogen, hydroxyl, aldehyde, keto, thiol, $CF_3$, nitro, nitroso, cyano, thiocyano, isocyanates, carbodiimide, carbamate, thiocarbamate, dithiocarbamate, amino, amido, imino, ammonium, silyl, sulphonate (—$SO_3^-$), —$OSO_3^-$, —$PO_3^-$ or —$OPO_3^-$, acyl, acyloxy or represents alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylamino-, alkylthio-, arylthio, alkylsulfonyl, alkylsulfinyl, dialkylamino, alkylammonium, alkylsilyl or alkoxysilyl, where these radicals may each optionally all be substituted by one or more aforementioned groups defined for $R^1$-$R^6$, or alternatively in each case two directly adjacent radicals from the group of $R^1$-$R^6$, including the ring carbon atoms to which they are attached by a cyclic bridging group, generating one or more cyclic structures, including aromatic structures.

or alternatively $R^6$ is optionally bridged with a different ligand of metal carbene complex catalyst, $C_1$-$C_6$ alkyl is, but not limited to, for example methyl, ethyl, n-propyl, iso-propyl, n-butyl, sec-butyl, tert-butyl, n-pentyl, 1-methylbutyl, 2-methylbutyl, 3-methylbutyl, neopentyl, 1-ethyl-propyl and n-hexyl.

$C_3$-$C_8$ cycloalkyl includes, but not limited to, cyclopropyl, cyclobutyl, cyclopentyl, cyclohexyl, cycloheptyl and cyclooctyl.

$C_6$-$C_{24}$ aryl includes an aromatic radical having 6 to 24 skeletal carbon atoms. Preferred mono-, bi- or tricyclic carbocyclic aromatic radicals have 6 to 10 skeletal carbon atoms, for example but not limited to, phenyl, biphenyl, naphthyl, phenanthrenyl or anthracenyl.

$X^1$ and $X^2$ are identical or different and represent two ligands, preferably anionic ligands.

In the general formulas can $X^1$ and $X^2$, for example, hydrogen, halogen, pseudohalogen, straight-chain or branched $C_1$-$C_{30}$ alkyl, $C_6$-$C_{24}$ aryl, $C_1$-$C_{20}$ alkoxy, $C_6$-$C_{24}$ aryloxy, $C_3$-$C_{20}$ alkyl diketonate, $C_6$-$C_{24}$ aryl diketonate, $C_1$-$C_{20}$ carboxylate, $C_1$-$C_{20}$ alkylsulfonate, $C_6$-$C_{24}$ aryl sulfonate, $C_1$-$C_{20}$ alkyl thiol, $C_6$-$C_{24}$ aryl thiol, $C_1$-$C_{20}$ alkylsulfonyl or $C_1$-$C_{20}$ alkylsulfinyl-radicals.

The abovementioned radicals $X^1$ and $X^2$ may further be substituted by one or more additional residues, for example by halogen, preferably fluorine, $C_1$-$C_{20}$ alkyl, $C_1$-$C_{20}$-alkoxy or $C_6$-$C_{24}$ aryl, where these groups may optionally be in turn be substituted by one or more substituents from the group comprising halogen, preferable fluorine, $C_1$-$C_5$ alkyl, $C_1$-$C_5$ alkoxy, and phenyl.

$X^1$ and $X^2$ may be joined to form a dianionic group and may form single ring of up to 30 non-hydrogen atoms or a multinuclear ring system of up to 30 non-hydrogen atoms.

$L^1$ and $X^1$ may be joined to form a multidentate mono-anionic group and may form single ring of up to 30 non-hydrogen atoms or a multinuclear ring system of up to 30 non-hydrogen atoms;

In a preferred embodiment, $X^1$ and $X^2$ are identical or different and denote halogen, in particular, fluorine, chlorine, bromine or iodine, benzoate, $C_1$-$C_5$ carboxylate, $C_1$-$C_5$ alkyl, phenoxy, $C_1$-$C_5$ alkoxy, $C_1$-$C_5$ alkyl thiol, $C_6$-$C_{24}$ arylthiol, $C_6$-$C_{24}$aryl or $C_1$-$C_5$ alkyl sulfonate.

In a particularly preferred embodiment, $X^1$ and $X^2$ are identical and are chlorine, $CF_3COO$, $CH_3COO$, $CFH_2COO$, $(CH_3)_3CO$, $(CF_3)_2(CH_3)CO$, $(CF_3)(CH_3)_2CO$, PhO (phenoxy), $C_6F_5O$ (pentafluorophenoxy), MeO (methoxy), EtO (ethoxy), tosylate (p-$CH_3$—$C_6H_4$—$SO_3$), mesylate (2,4,6-trimethylphenyl) or $CF_3SO_3$ (trifluoromethanesulfonate).

$L^1$ and $L^2$ are identical or different ligands, preferably represent neutral electron donors, wherein $L^2$ can be bridged alternatively by a radical $R^6$, The two ligands $L^1$ and $L^2$ may, for example, independently of one another, representing a phosphine, sulphonated phosphine, phosphate, phosphinite, phosphonite, phosphite, arsine, stibine, ether, amine, amide, sulfoxide, carboxyl, nitrosyl, pyridine, substituted pyridine, pyrazine, thiocarbonyl, thioether, N-Heterocyclic carbene ("NHC"), substituted NHC, or cyclic alkyl amino carbene (CAAC) or substituted CAAC.

Preferably, the two ligands $L^1$ and $L^2$ independently of one another represents a phosphine ligand having the formula $P(L^3)_3$ with $L^3$ are identical or different and are alkyl, preferably $C_1$-$C_{10}$ alkyl, more preferably $C_1$-$C_5$-alkyl, cycloalkyl-, preferably $C_3$-$C_{20}$ cycloalkyl, more preferably $C_3$-$C_8$ cycloalkyl, preferably cyclopentyl, cyclohexyl, and neopentyl, aryl, preferably $C_6$-$C_{24}$ aryl, more preferably phenyl or toluyl, $C_1$-$C_{10}$ alkyl-phosphabicyclononane, $C_3$-$C_{20}$ cycloalkyl phospha-bicyclononane, a sulfonated phosphine ligand of formula $P(L^4)_3$ wherein $L^4$ represents a mono- or poly-sulfonated $L^3$-ligand; $C_6$-$C_{24}$ aryl or $C_1$-$C_{10}$ alkyl-phosphinite ligand, a $C_6$-$C_{24}$ aryl or $C_1$-$C_{10}$ alkyl phosphonite ligand, a $C_6$-$C_{24}$aryl or $C_1$-$C_{10}$ alkyl phosphite-ligand, a $C_6$-$C_{24}$ aryl $C_1$-$C_{10}$ alkyl arsine ligand, a $C_6$-$C_{24}$ aryl or $C_1$-$C_{10}$ alkyl amine ligands, a pyridine ligand, a $C_6$-$C_{24}$ aryl or $C_1$-$C_{10}$ alkyl-sulfoxide ligand, a $C_6$-$C_{24}$ aryl or $C_1$-$C_{10}$ alkyl ether ligand or a $C_6$-$C_{24}$ aryl or $C_1$-$C_{10}$ alkyl amide ligands which all can be multiply substituted, for example by a phenyl group, wherein these substituents are in turn optionally substituted by one or more halogen, $C_1$-$C_5$ alkyl or $C_1$-$C_5$ alkoxy radicals.

The term "phosphine" includes, for example, PPh$_3$, P(p-Tol)$_3$, P(o-Tol), PPh(CH$_3$)$_2$, P(CF$_3$)$_3$, P(p-FC$_6$H$_4$)$_3$, P(p-CF$_3$C$_6$H$_4$)$_3$, P(C$_6$H$_4$—SO$_3$Na)$_3$, P(CH$_2$C$_6$H$_4$—SO$_3$Na)$_3$, P(iso-Propyl)$_3$, P(CHCH$_3$(CH$_2$CH$_3$))$_3$, P(cyclopentyl)$_3$, P(cyclohexyl)$_3$, P(Neopentyl)$_3$ and cyclohexyl-phosphabicyclononane.

The term "phosphinite" includes for example Triphenylphosphinite, Tricyclohexylphosphinite, Triisopropylphosphinite and methyldiphenylphosphinite.

The term "phosphite" includes, for example, triphenyl phosphite, tricyclohexyl phosphite, tri-tert-butyl phosphite, triisopropyl phosphite and methyldiphenylphosphite.

The term "stibine" includes, for example triphenylstibine, tricyclohexylstibine and Trimethylstibene.

The term "sulfonate" includes, for example, trifluoromethanesulfonate, tosylate and mesylate.

The term "sulfoxide" includes, for example, CH$_3$S(=O)CH$_3$ and (C$_6$H$_5$)$_2$SO.

The term "thioether" includes, for example CH$_3$SCH$_3$, C$_6$H$_5$SCH$_3$, CH$_3$OCH$_2$CH$_2$SCH$_3$ and tetra-hydrothiophene.

The term "pyridine" in this application is a generic term and include all the nitrogen-containing ligands described by Grubbs in WO-A-03/011455 but not limited to. Examples are: pyridine, picolines (α-, β-, and γ-picoline), lutidines (2,3-, 2,4-, 2,5-, 2,6-, 3,4- and 3,5-lutidine), collidine (2,4,6-trimethylpyridine), trifluoromethylpyridine, phenylpyridine, 4-(dimethylamino) pyridine, chloropyridines (2-, 3- and 4-chloropyridine), bromopyridines (2-, 3- and 4-bromopyridine), nitropyridines (2-, 3- and 4-nitropyridine), quinoline, pyrimidine, pyrrole, imidazole and phenylimidazole.

The N-Heterocyclic carbene (NHC) has usually a structure of the formulas (IIa) or (IIb):

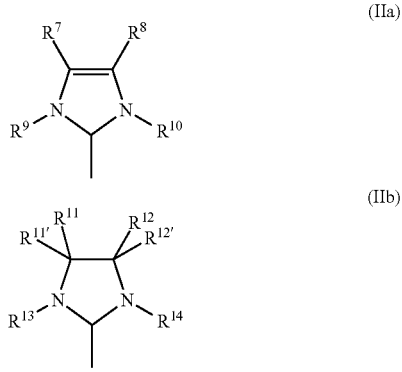

by which
$R^7$-$R^{14}$, $R^{11'}$, $R^{12'}$ are identical or different and are hydrogen, halogen, hydroxyl, aldehyde, keto, thiol, CF$_3$, nitro, nitroso, cyano, thiocyano, isocyanates, carbodiimide, carbamate, thiocarbamate, dithiocarbamate, amino, amido, imino, ammonium, silyl, sulphonate (—SO$_3^-$), —OSO$_3^-$, —PO$_3^-$ or —OPO$_3^-$, acyl, acyloxy or represents alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylammonium, alkylamino-, alkylthio-, arylthio, alkylsulfonyl, alkylsulfinyl, dialkylamino, alkylsilyl or alkoxysilyl, where these radicals may each optionally all be substituted by one or more aforementioned groups defined for $R^1$-$R^6$, Optionally, one or more of the radicals $R^7$-$R^{14}$, $R^{11'}$, $R^{12'}$ independently of one another can be substituted by one or more substituents, preferably straight or branched C$_1$-C$_{10}$ alkyl, C$_3$-C$_8$ cycloalkyl, C$_1$-C$_{10}$ alkoxy or C$_6$-C$_{24}$ aryl, where these aforementioned substituents may in turn be substituted by one or more radicals, preferably selected from the group comprising halogen, especially chlorine or bromine, C$_1$-C$_5$ alkyl, C$_1$-C$_5$ alkoxy and phenyl.

Just for clarification, the depicted structures of the N-Heterocyclic carbene in the general formulas (IIa) and (IIb) are equal with the N-Heterocyclic carbenes described in the literature, where frequently the structures (IIa') and (IIb') are used, which highlighting the carbene character of N-Heterocyclic carbene. This also applies to the corresponding preferred, structures shown below (IIIa)-(IIIf):

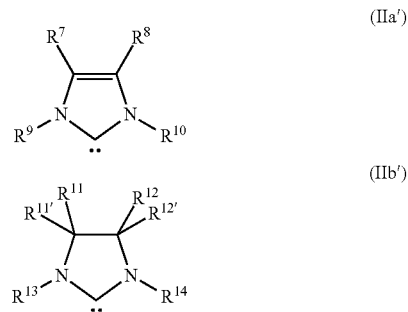

In a preferred embodiment of the catalysts of the general formulas (IIa) and (IIb) $R^7$, $R^8$, $R^{11}$, $R^{11'}$, $R^{12}$ and $R^{12'}$ are independently of one another denote hydrogen, C$_6$-C$_{24}$-aryl, particularly preferably phenyl, straight or branched C$_1$-C$_{10}$ alkyl, particularly preferably propyl or butyl, or together with the inclusion of the carbon atoms to which they are attached form a cycloalkyl or aryl radical, where all the abovementioned radicals are optionally substituted may be substituted by one or more further radicals selected from the group comprising straight or branched C$_1$-C$_{10}$ alkyl, C$_1$-C$_{10}$ alkoxy, C$_6$-C$_{24}$ aryl, and a functional group selected from the group consisting of hydroxy, thiol, thioether, ketone, aldehyde, ester, ether, amine, imine, amide, nitro, carboxylic acid, disulfide, carbonate, isocyanate, carbodiimide, carboalkoxy, carbamate, and halogen.

In a particularly preferred embodiment, the catalysts of the general formulas (IIa) and (IIb) have one or two N-Heterocyclic carbene (NHC) as ligands L$^1$ and L$^2$, where the radicals $R^9$, $R^{10}$, $R^{13}$ and $R^{14}$ are identical or different and are straight or branched C$_1$-C$_{10}$ alkyl, particularly preferably i-propyl or neopentyl, C$_3$-C$_{10}$ cycloalkyl, preferably adamantyl, C$_6$-C$_{24}$ aryl, particularly preferably phenyl, C$_1$-C$_{10}$ alkylsulfonate, particularly preferably methanesulphonate, C$_1$-C$_{10}$ arylsulphonate, particularly preferably p-toluenesulfonate.

If necessary, the above-mentioned residues are substituted as the meanings of $R^9$, $R^{10}$, $R^{13}$ and $R^{14}$ by one or more further radicals selected from the group comprising straight or branched C$_1$-C$_5$ alkyl, especially methyl, C$_1$-C$_5$ alkoxy, aryl and a functional group selected from the group consisting of hydroxy, thiol, thioether, ketone, aldehyde, ester, ether, amine imine, amide, nitro, carboxylic acid, disulfide, carbonate, isocyanate, carbodiimide, carboalkoxy, carbamate, and halogen.

In particular, the radicals $R^9$, $R^{10}$, $R^{13}$ and $R^{14}$ can be identical or different and denote i-propyl, neopentyl, adamantyl, mesityl or 2,6-diisopropylphenyl.

Particularly preferred N-Heterocyclic carbenes (NHC) have the following structure (IIIa)-(IIIf), with measurements for each one is 2,4,6-trimethylphenyl radical or alternatively, in all cases, for a 2,6-diisopropylphenyl radical.

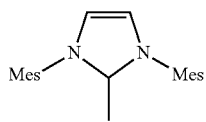
(IIIa)

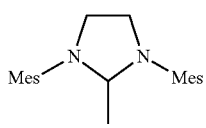
(IIIb)

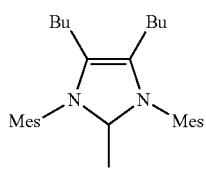
(IIIc)

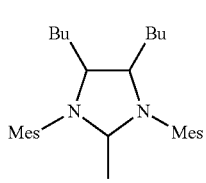
(IIId)

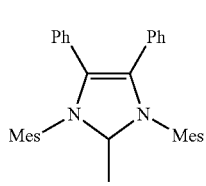
(IIIe)

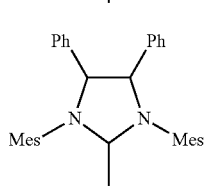
(IIIf)

In other useful embodiments, one of the N groups bound to the carbene in Formulae (IIa) or (IIb) is replaced with another heteroatom, preferably S, O or P, preferably an S heteroatom. Other useful N-heterocyclic carbenes include the compounds described in Hermann, W A. *Chem. Eur. J* 1996, 2, 772 and 1627; Enders, D. et al., *Angew. Chem. Int. Ed.* 1995, 34, 1021; Alder R. W., *Angew. Chem. Int. Ed.* 1996, 35, 1121; and Bertrand, G. et al., *Chem. Rev.* 2000, 100, 39.

For purposes of this invention and claims thereto, "cyclic alkyl amino carbenes" (CAACs) are represented by the Formula (IV):

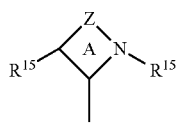
(IV)

Wherein the ring A is a 4-, 5-, 6-, or 7-membered ring, and Z is a linking group comprising from one to four linked vertex atoms selected from the group comprising C, O, N, B, Al, P, S and Si with available valences optionally occupied by hydrogen, oxo or R-substituents, wherein R is independently selected from the group comprising $C_1$ to $C_{12}$ hydrocarbyl groups, substituted $C_1$ to $C_{12}$ hydrocarbyl groups, and halides, and each $R_{15}$ is independently a hydrocarbyl group or substituted hydrocarbyl group having 1 to 40 carbon atoms, preferably methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluyl, chlorophenyl, phenol, or substituted phenol.

Some particularly useful CAACs include:

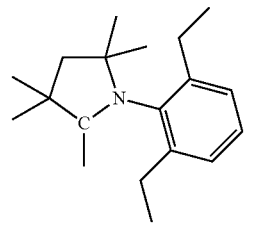

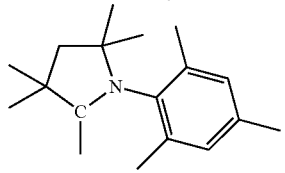

Other useful CAACs include the compounds described in U.S. Pat. No. 7,312,331 and Bertrand et al, *Angew. Chem. Int. Ed.* 2005, 44, 7236-7239.

For the case that the radical $R^6$ is bridged to another ligand of the inventive catalyst with the general formula (I), the following examples can be generated with the structures of the general formula (V).

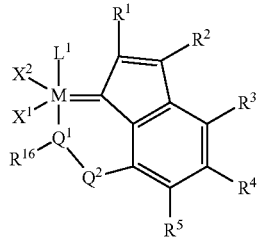
(V)

$Q^1$ is oxygen, sulfur, a radical N—$R^{17}$ or P—$R^{17}$, wherein $R^{17}$ has the following meaning, $R^{16}$ and $R^{17}$, are equal or different, and can be an alkyl, cycloalkyl, alkenyl, alkynyl, aryl, alkoxy, alkenyloxy, alkynyloxy, aryloxy, alkoxycarbonyl, alkylamine, alkylammonium, alkylthio, arylthio, alkylsulfonyl or alkylsulphinyl radical, all of which may each optionally be substituted by one or more alkyl, halogen, alkoxy, aryl or heteroaryl radicals. $R^{16}$ and $R^{17}$ can be linked together generating cyclic structures.

$Q^2$ is —$(CH_2)_r$— with r=1, 2 or 3, —C(=O)—$CH_2$—, —C(=O)—, —N=CH—, —N(H)—C(=O)—, —(CHR$^{18}$)—, —(CR$^{18}$R$^{19}$)— or, alternatively, the entire structural unit "Q$^1$(R$^{16}$)-Q$^2$" is one of the following groups (—N(R$^{16}$)=CH—CH$_2$—), (—N(R$^{16}$, R$^{17}$)=CH—CH$_2$—) group, and wherein R$^{18}$ and R$^{19}$ has the same meaning as R$^{16}$ and R$^{17}$. In addition two or more R-radicals selected from R$^{16}$, R$^{17}$, R$^{18}$ or R$^{19}$ can be linked together generating cyclic structures.

wherein M, X$^1$, X$^2$, L$^1$, R$^1$-R$^5$ have the same meanings as in the general formula (I).

As examples of the catalysts of the invention, the following structures may be mentioned:

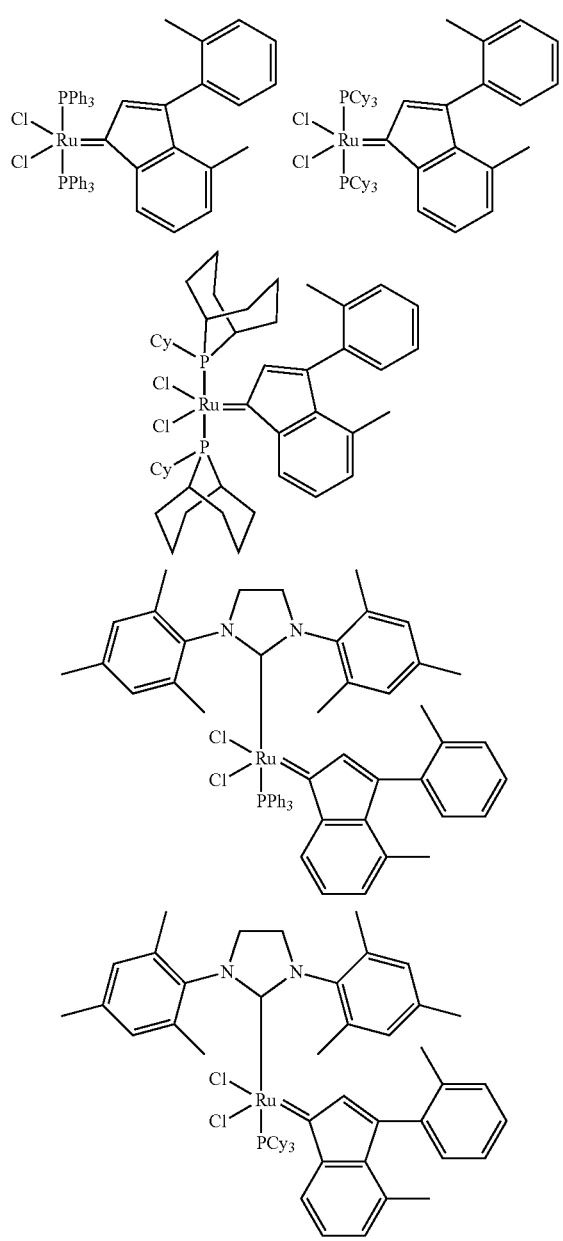

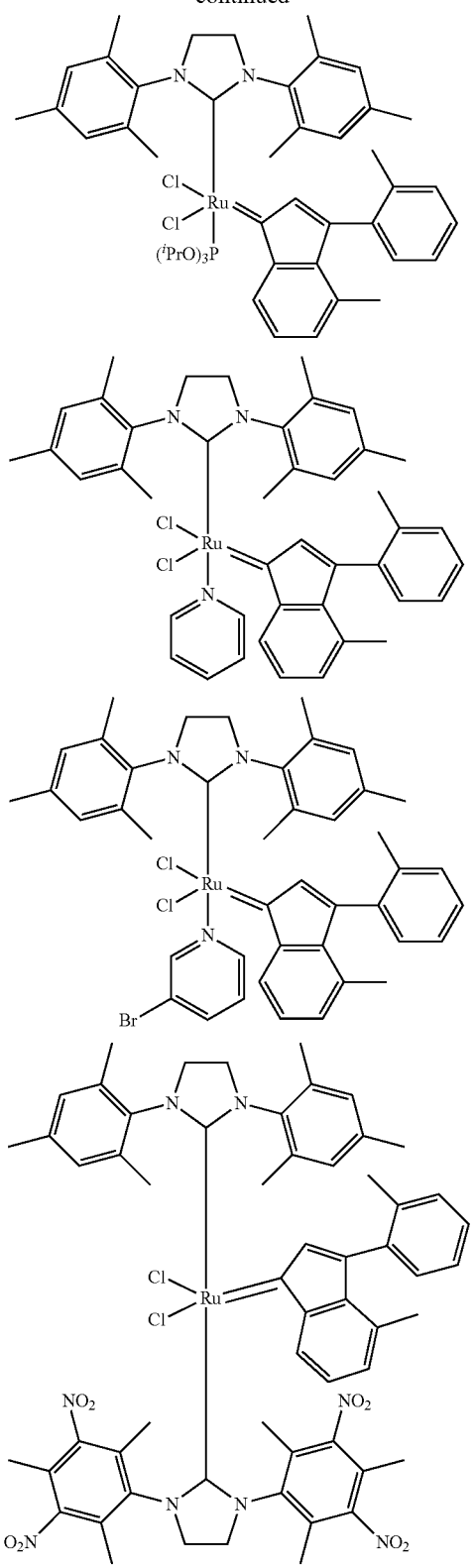

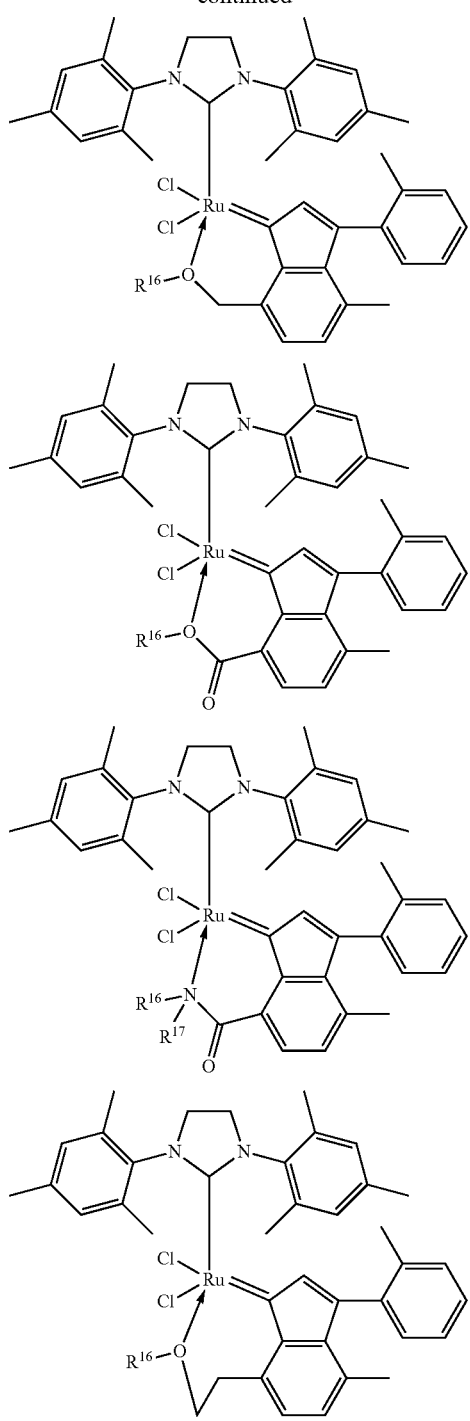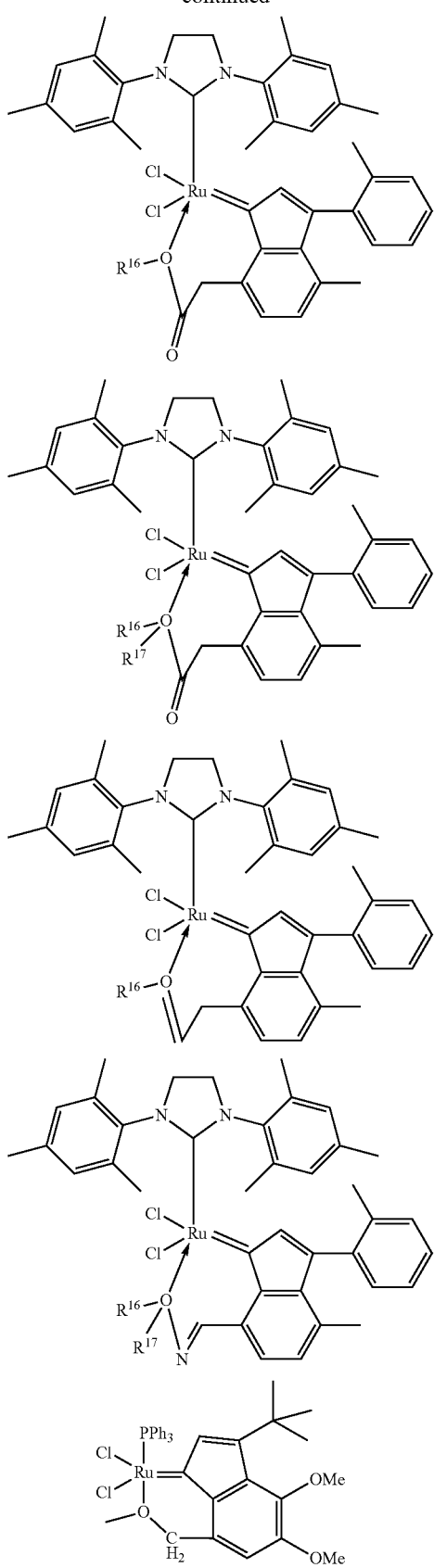

-continued

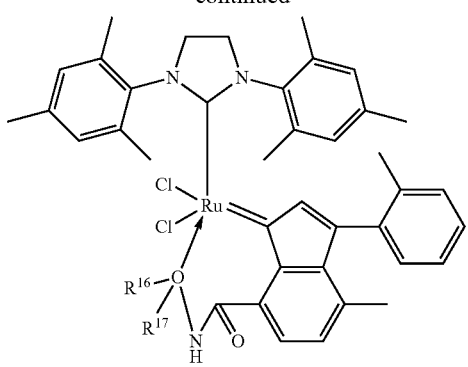

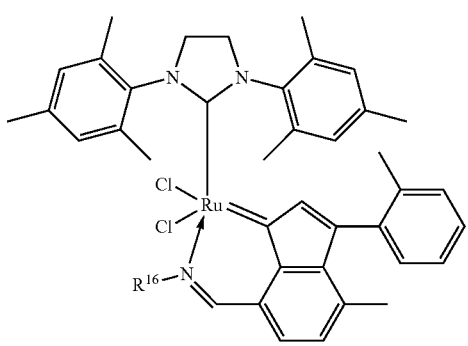

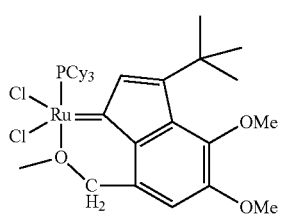

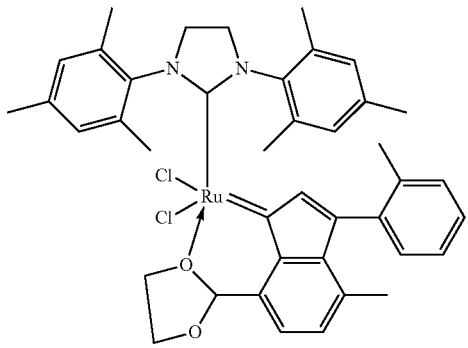

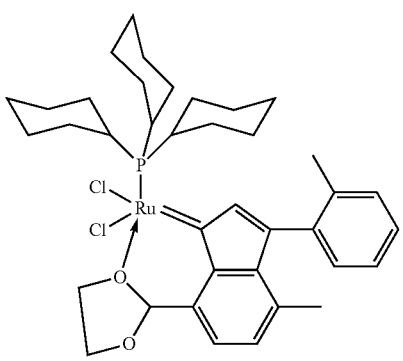

-continued

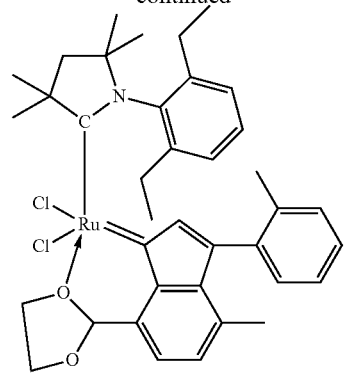

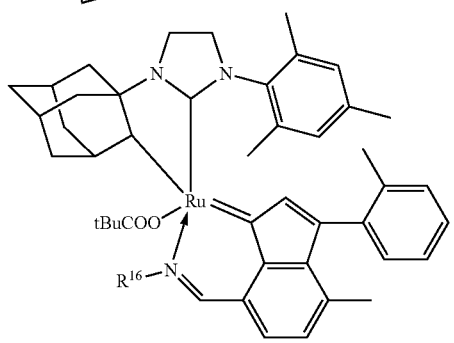

In certain embodiments, the catalyst compound employed in the olefin metathesis processes may be bound to or deposited on a solid catalyst support. The solid catalyst support will make the catalyst compound heterogeneous, which will simplify catalyst recovery. In addition, the catalyst support may increase catalyst strength and attrition resistance. Suitable catalyst supports include, without limitation, silica's, alumina's, silicaalumina's, aluminosilicates, including zeolites and other crystalline porousaluminosilicates; as well as titania's, zirconia, magnesium oxide, carbon, and cross-linked, reticular polymeric resins, such as functionalized cross-linked polystyrenes, e.g., chloromethyl-functionalized cross-linked polystyrenes. The catalyst compound may be deposited onto the support by any method known to those skilled in the art, including, for example, impregnation, ion-exchange, deposition-precipitation, and vapor deposition. Alternatively, the catalyst compound may be chemically bound to the support via one or more covalent chemical bonds, for example, the catalyst compound may be immobilized by one or more covalent bonds with one or more of substituents of the indenylidene ligand or directly immobilized via one or more chemical bounds on the Group 8 metal by substituting one or more anionic ligands or immobilized via one or more chemical bounds between the $L^1$ ligand and the support.

If a catalyst support is used, the catalyst compound may be loaded onto the catalyst support in any amount, provided that the metathesis process proceeds to the desired metathesis products. Generally, the catalyst compound is loaded onto the support in an amount that is greater than about 0.01 wt % of the Group 8 metal, based on the total weight of the catalyst compound plus support. Generally, the catalyst compound is loaded onto the support in an amount that is less than about 20 wt % of the Group 8 metal, based on the total weight of the catalyst compound and support.

In general, acetylenic compounds useful in this invention may contain a chelating moiety of the formula (VI)

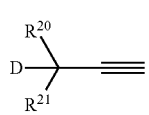

(VI)

wherein,

D is a leaving group;

$R^{20}$ to $R^{21}$ are as defined below, and may contain $R^{16}$-$Q^1$-$Q^2$;

$R^{20}$ is selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, and wherein when $R^{20}$ is aryl, polyaryl, or heteroaryl, $R^{20}$ may be substituted with any combination of $R^1$, $R^2$, $R^3$, $R^4$, $R^5$, and $R^6$ and can be linked with any of $R^1$, $R^2$, $R^3$, $R^4$, $R^5$, and $R^6$ to form one or more cyclic aromatic or non-aromatic groups.

$R^{21}$ is selected from annulenes, having the general formula $C_nH_n$ (when n is an even number) or $C_nH_{n+1}$ (when n is an odd number). Well-know representative compounds of annulenes, but not limited, are cyclobutadiene, benzene, and cyclooctatetraene. Annulenes can be aromatic or anti-aromatic. Every H-atom from the annulene fragment can be substituted by halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, and wherein when $R^{21}$ is aryl, polyaryl, or heteroaryl, $R^{21}$ may be substituted with any combination of $R^1$, $R^2$, $R^3$, $R^4$, $R^5$, and can be linked with any of $R^1$, $R^2$, $R^3$, $R^4$, $R^5$ and $R^6$ to form one or more cyclic aromatic or non-aromatic groups.

Examples of suitable leaving groups include, but are not limited to, hydroxyl, halide, ester, perhalogenated phenyl, acetate, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, D is selected from hydroxyl, halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In particular embodiments, D is advantageously hydroxyl (OH).

Preferred organic acetylenic compounds are of the formula (VII),

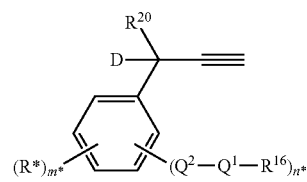

(VII)

Wherein $Q^1$, $Q^2$ and $R^{16}$ are as defined above;

n* is an integer from 0 to 5;

m* is an integer from 1 to 5; and m*=5−n*

R* is selected from $R^1$, $R^2$, $R^3$, $R^4$, $R^5$ and $R^6$, or combinations thereof, as defined above.

D and $R^{20}$ are as defined above.

Preferred organic acetylenic compounds include

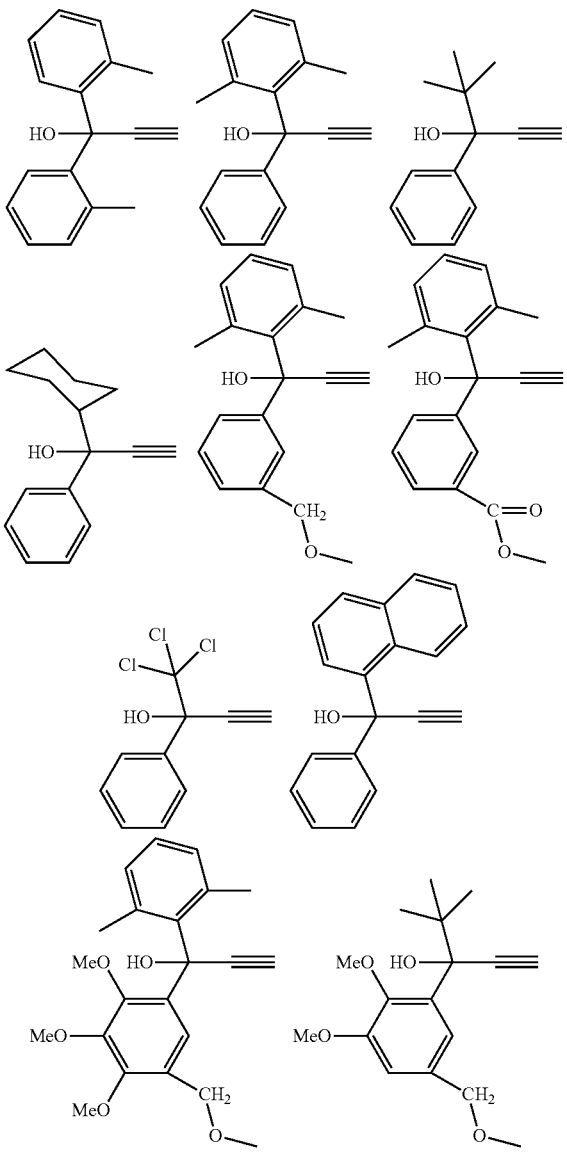

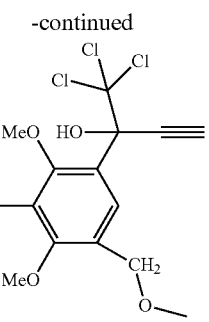

Synthesis of Metathesis Catalyst Compounds

The catalyst compounds described in this invention may be synthesized by any methods known to those skilled in the art.

Representative methods of synthesizing the Group 8 catalyst compound of the type described herein include, for example, treating a solution of the ligand in a suitable solvent, such as dioxane, with a reactant complex of a Group 8 metal, such as dichlorobis-(triphenylphosphine)ruthenium (II) and hydrogen chloride (in dioxane). The reaction mixture may be heated, for a time period appropriate to yield the desired modified indenylidene catalyst compound. Typically, removal of the volatiles and washed with hexane affords the Group 8 modified indenylidene catalyst compound in high yields.

A phosphine ligand, such as tricyclohexylphosphine, cyclohexyl-phosphabicyclononane, a phosphinite or a phosphinite may be added thereafter, if desired. The reaction conditions typically include mixing the Group 8 reactant catalyst compound and the preferred phosphine ligand in a suitable solvent, e.g. dichloromethane, for a time sufficient to effectuate the phosphine ligand exchange, at a suitable temperature typically ambient.

In case of an exchange of phosphine ligands, the characteristic NMR-value of the H atom at C8 and of the P of the new compounds will be given.

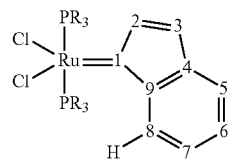

While the present invention describes a variety of transition metal complexes useful in catalyzing metathesis reactions, it should be noted that such complexes may be formed in situ. Accordingly, additional ligands may be added to a reaction solution as separate compounds, or may be complexed to the metal center to form a metal-ligand complex prior to introduction to the reaction.

Synthetic protocols for representative 1,1-substituted prop-2-yn-1-ol ligands and the corresponding ruthenium alkylidene complexes are as follows. Other substituted prop-2-yn-1-ol ligands and their respective metal complexes may be derived analogously.

Example 1: Synthesis of (PPh$_3$)$_2$Cl$_2$Ru(3-2-methylphenyl-5-methylinden-1-ylidene)

Scheme 1: Synthesis of (PPh$_3$)$_2$Cl$_2$Ru(3-2-methylphenyl-5-methylinden-1-ylidene) (1D)

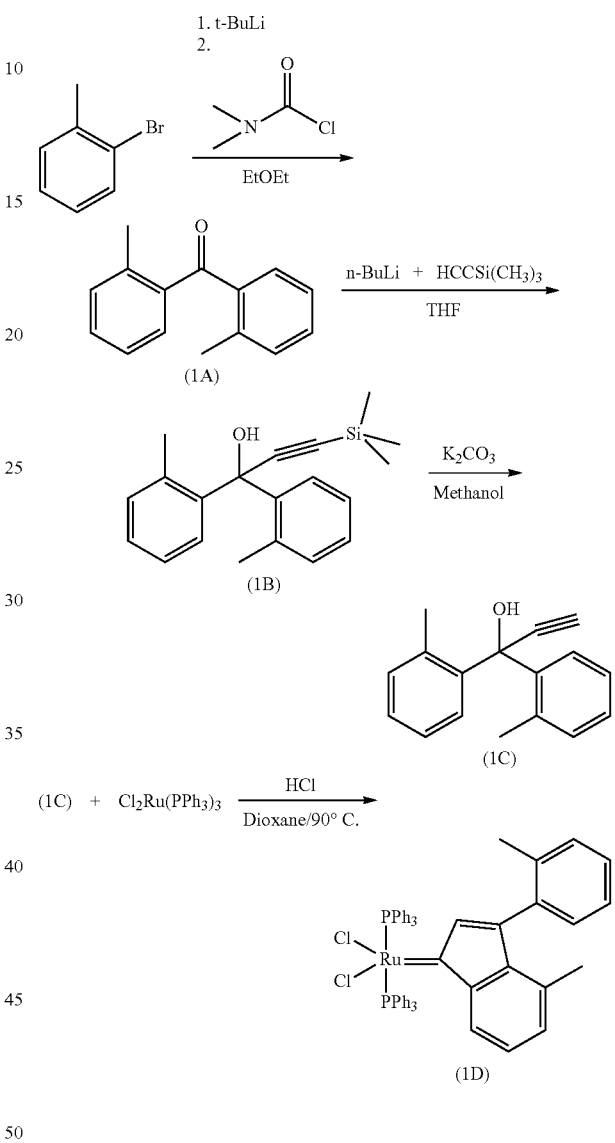

Step 1: Bis(2-methylphenyl)methanone (1A)

To a solution of 2-bromotoluene (2 eq., 2.6 ml, 21.79 mmol,) in 26 ml diethyl ether at −90° C., t-BuLi (1.9 M in pentane) (3 eq., 32.7 mmol, 17.2 ml.) was added drop wise. The solution was stirred for 30 min. at room temperature, followed by drop wise addition of N,N-dimethylcarbamoyl chloride (1 eq., 1 ml, 10.9 mmol), the reaction mixture was stirred for another 3 hours. The crude reaction mixture was quenched using 35 ml 1N HCl and diluted with diethyl ether. The organic phase was washed with water and the aqueous phase was extracted twice with diethyl ether, thereafter the ether fractions were combined and dried with anhydrous MgSO$_4$. Removal of MgSO$_4$ by filtration followed by purification using flash column chromatography (silica gel, hexane as solvent) and finally evaporation of the solvent and a white solid was obtained 0.93 g (40.6%).

¹H NMR (300 MHz, CDCl₃, TMS): δ 7.38 (td, 2H), 7.29 (td, 4H), 7.20 (td, 2H), 2.44 (s, 6H).
¹³C NMR (75 MHz, CDCl₃): δ 200.79, 139.01, 138.17, 131.43, 131.07, 130.31, 125.42, 20.67.

Step 2: 1,1-bis-methylphenyl-3-(trimethylsilyl)prop-2-yn-1-ol (1B)

n-BuLi (2.5 M in hexanes) (1.5 eq., 5.7 ml, 14.28 mmol,) was added drop wise to stirred solution of trimethylsily-lacetylene (1.5 eq., 2 ml, 14.28 mmol) in anhydrous THF (17 ml) at −90° C. under an argon atmosphere. After addition, the resulting solution was stirred for another 5 min in a cold bath followed by stirring for 30 minutes at room temperature. Thereafter, bis(2-methylphenyl)methanone (9.52 mmol, 2 g) in 17 ml dry THF was added slowly to the solution at −90° C. and the resulting mixture was allowed to heat up and refluxed for 30 min. The crude reaction mixture was quenched using 15 ml 1N HCl and diluted with diethyl ether. The organic phase was washed with water and the aqueous phase were combined and extracted twice with ether, thereafter the ether fractions were combined and dried with anhydrous MgSO₄. After removal of MgSO₄ by filtration, and evaporation of the solvent a yellow liquid was obtained in quantitative yield. The obtained product was used without further purification.
¹H NMR (300 MHz, CDCl₃, TMS): δ 7.95 (dd, 2H), 7.27 (dd, 4H), 7.15 (dd, 2H) 2.75 (s, 1H) 2.14 (s, 6H), 0.27 (d, 9H).
¹³C NMR (75 MHz, CDCl₃): δ 141.01, 136.76, 132.37, 128.13, 127.45, 125.58, 107.10, 92.44, 75.01, 21.40, 0.00.

Step 3: 1,1-bis-2-methylphenyl-prop-2-yn-1-ol (1C)

A solution of 1,1-bis-methylphenyl-3-(trimethylsilyl)prop-2-yn-1-ol was obtained from previous step and K₂CO₃ (1 eq, 1.3 g 9.52 mmol) in dry methanol (10 ml) was stirred at room temperature for 3 h. The crude reaction mixture was quenched using 20 ml 1N HCl and diluted with diethyl ether. The organic phase was washed with water and the aqueous phase was extracted twice with diethyl ether, thereafter the ether fractions were combined and dried on anhydrous MgSO₄. Removal of MgSO₄ by filtration followed by purification using flash column chromatography (silica gel, Hexane/EtOAc=30/1) and finally evaporation of the solvent a yellowish solid (2.06 g, 92% yield for step 2+3) was obtained.
¹H NMR (300 MHz, CDCl₃, TMS): δ 7.95 (m, 2H), 7.23 (m, 4H), 7.09 (m, 2H) 2.89 (s, 1H) 2.67 (s, 1H), 2.02 (s, 6H).
¹³C NMR (75 MHz, CDCl₃): δ 140.60, 136.33, 132.30, 128.19, 127.24, 125.58, 85.52, 76.80, 74.75, 21.16.
ESI [M-OH]: 219.1, calculated: 219.1.

Step 4: (PPh₃)₂Cl₂Ru(3-2-methylphenyl-5-methylphenyl-inden-1-ylidene) (1D)

(PPh₃)₃RuCl₂ (1 eq., 0.575 g, 0.6 mmol) and 1,1-bis-2-methylphenyl-prop-2-yn-1-ol (compound C, 1.5 eq., 0.213 g, 0.9 mmol) were added in 4 ml HCl/dioxane solution (0.15 mol/l). The solution was heated to 90° C. for 3 hour, after which the solvent was removed under vacuum. Hexane (20 ml) was added to the flask and the solid was ultrasonically removed from the wall. The resulting suspension was filtered and washed two times using hexane (5 ml). The remaining solvent was evaporated affording a red-brown powder; 0.52 g (Yield: 95%). The product was characterized by NMR spectra ¹H and ³¹P.

¹H NMR (300 MHz, CDCl₃, TMS): δ 7.56 (dd, 11H), 7.37 (t, 6H), 7.21-7.31 (m, 13H), 7.09 (tetra, 3H), 6.95 (t, 3H), 6.47 (t, 1H), 6.14 (s, 1H), 2.20 (s, 3H), 1.66 (s, 3H).
³¹P NMR (121.49 MHz, CDCl₃): δ 29.33.

Example 2: Synthesis of (PPh₃)₂Cl₂Ru(3-2-methoxyphenyl-5-methoxyinden-1-ylidene)

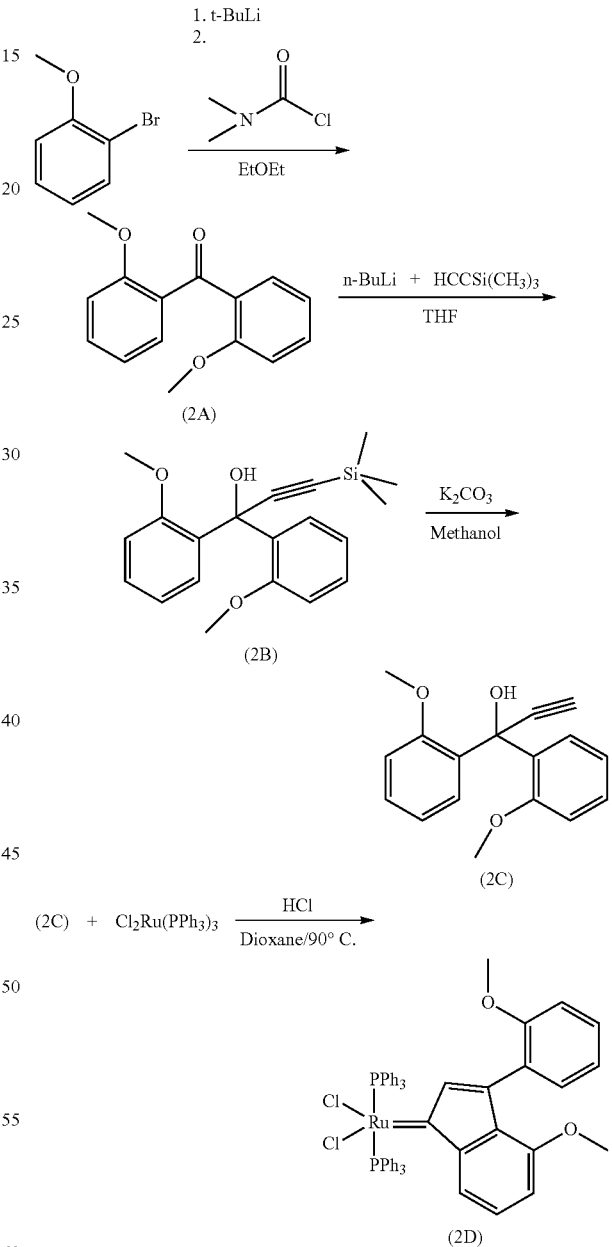

Step 1: Bis(2-methoxyphenyl)methanone (2A)

To a suspension of 2-Bromoanisole (2 eq., 6.61 g, 35.4 mmol) in 42 ml dry diethyl ether at −90° C., a solution of t-BuLi (1.9 M in pentane) (2.6 eq., 24.2 ml, 46.0 mmol) was added drop wise. The solution was allowed to warm up to room temperature. After half hour N,N-dimethylcarbamoyl chloride (1 eq., 1.9 g, 17.7 mmol) was added drop wise and the reaction mixture was stirred for another 3 hours. The crude reaction mixture was quenched using 50 ml 1N HCl and diluted with diethyl ether. The organic phase was washed with water and the aqueous phase was extracted twice with ether, thereafter the ether fractions were combined and dried with anhydrous MgSO$_4$. The crude product was purified by flash column chromatography (silica gel, Hexane/EtOAc=8:1) to afford a white solid 4.11 g (Yield: 96.0%).

$^1$H NMR (300 MHz, CDCl$_3$): δ 7.51 (dd, 2H), 7.41 (m, 2H), 6.97 (td, 2H), 6.90 (d, 2H), 3.64 (s, 6H).

$^{13}$C NMR: δ 195.35, 158.32, 132.64, 130.38, 120.34, 111.49, 55.68.

Step 2: 1,1-bis(2-methoxyphenyl)-3-(trimethylsilyl)prop-2-yn-1-ol (2B)

n-BuLi (2.5 M in hexanes) (1.5 eq., 6.6 ml, 16.6 mmol,) was added drop wise to a stirred solution of trimethylsilylacetylene (1.1 eq., 2 ml, 14 mmol) in anhydrous THF (23 ml) at −90° C. under an inert atmosphere. After addition, the resulting solution was stirred for 5 min in a cold bath and 30 minutes at room temperature. Thereafter, bis(2-methoxyphenyl)methanone (1 eq, 3.1 g, 12.7 mmol) in 23 ml dry THF was added slowly to the trimethylsilylacetylene solution at −90° C. and the resulting mixture was allowed to heat up and refluxed for 30 min. The crude reaction mixture was quenched with 17 ml 1N HCl and diluted with diethyl ether. The organic phase was washed with water and the aqueous phase were combined and extracted twice with ether, thereafter the ether fractions were combined and dried with anhydrous MgSO$_4$.

After removal of MgSO$_4$ by filtration, and evaporation of the solvent an oily liquid was obtained in quantitative yield. The obtained product was used without further purification.

Step 3: 1,1-bis-2-methoxyphenyl-prop-2-yn-1-ol (2C)

A solution of 1,1-bis(2-methoxyphenyl)-3-(trimethylsilyl)prop-2-yn-1-ol (obtained from previous step) and K$_2$CO$_3$ (1 eq., 1.75 g, 12.7 mmol) in dry methanol (14 ml) was stirred at room temperature for 3 h. After completion of the reaction (monitored using TLC), methanol was removed and 150 ml diethyl ether and 30 ml water were added. After separation of the 2 phases, the aqueous phase was extracted three times with 50 ml diethyl ether. Thereafter, the ether fractions were combined, concentrated followed by addition of 30 ml acetone and dried on anhydrous MgSO$_4$. Removal of MgSO$_4$ by filtration followed by purification using flash column chromatography (silica gel, Hexane/EtOAc=3:1) and finally evaporation of the solvent a white solid (2.8 g, yield 82.1% for step 2+3) was obtained.

$^1$H NMR (300 MHz, CDCl$_3$): δ 7.67 (dd, 2H), 7.27 (m, 2H), 6.98 (td, 2H), 6.88 (dd, 2H), 5.09 (s, 1H), 3.66 (s, 6H), 2.73 (s, 1H).

$^{13}$C NMR: δ 156.66, 131.55, 129.07, 128.05, 120.50, 112.43, 86.23, 73.28, 72.93, 55.76.

Step 4: (PPh$_3$)$_2$Cl$_2$Ru(3-2-methoxyphenyl-5-methoxyphenyl-inden-1-ylidene 2D (PPh$_3$)$_3$RuCl$_2$ (1 eq., 0.575 g, 0.6 mmol) and 1,1-bis-2-methoxyphenyl-prop-2-yn-1-ol (compound C, 1.5 eq., 0.241 g, 0.9 mmol) were added in 4 ml HCl/dioxane solution (0.15 mol/l). The solution was heated to 90° C. for 3 hour, after which the solvent was removed under vacuum. Hexane (20 ml) was added to the flask and the solid was ultrasonically removed from the wall. The resulting suspension was filtered and washed two times using hexane (5 ml). The remaining solvent was evaporated affording a red-brown powder; 0.53 g (Yield: 93%). The product was characterized by NMR spectra $^{31}$P.

$^{31}$P NMR (121.49 MHz, CDCl$_3$): δ 28.76.

Example 3: Synthesis of (PPh$_3$)$_2$Cl$_2$Ru(3-t-butyl-inden-1-ylidene)

Scheme 3: Synthesis of (PPh3)2Cl2Ru(3-t-butyl-inden-1-ylidene) (3C)

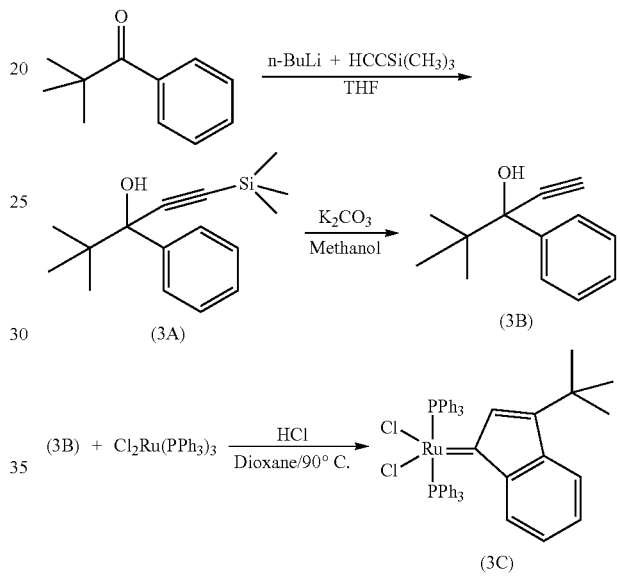

Step 1: 1-t-butyl-1-phenyl-3-(trimethylsilyl)prop-2-yn-1-ol (3A)

n-BuLi (2.5 M in hexane) (1.2 eq., 2.96 ml, 7.4 mmol) was added drop wise to a cold solution (−90° C.) of trimethylsilylacetylene (1.2 eq., 1.1 ml, 7.4 mmol) in anhydrous THF (21 ml) under a argon atmosphere. After addition, the resulting solution was stirred for another 5 min in a cold bath and 30 minutes at room temperature. Thereafter, 2,2-dimethyl-1-phenylpropan-1-one (1 eq., 1 g, 6.17 mmol) in 21 ml dry THF was added slowly to the trimethylsilylacetylene solution at −90° C. and the resulting mixture was allowed to heat up and refluxed for 30 min. The crude reaction mixture was quenched using 10 ml 1N HCl and diluted with diethyl ether. The organic phase was washed with water and the aqueous phase were combined and extracted twice with ether, thereafter the ether fractions were combined and dried on anhydrous MgSO$_4$. After removal of MgSO$_4$ by filtration, and evaporation of the solvent a oily liquid was obtained in quantitative yield. The obtained product was used without further purification.

Step 2: 1-t-Butyl-1-phenyl-prop-2-yn-1-ol (3B)

A solution 1-t-butyl-1-phenyl-3-(trimethylsilyl)prop-2-yn-1-ol (obtained from previous step) and K$_2$CO$_3$ (1 eq., 6.17 mmol, 0.85 g) in dry methanol (7 ml) was stirred at room temperature for 3 h. Afterwards the crude reaction mixture was quenched using 15 ml 1N HCl and diluted with diethyl ether. The organic phase was separated and washed with water, the aqueous phases were combined and extracted twice with ether, once with $CH_2Cl_2$. Subsequently the organic fractions were combined and dried on $MgSO_4$. Removal of $MgSO_4$ by filtration, the solvent was evaporated and an oil was obtained with high purity 1.06 g (yield 91.3%, step 1+2).

$^1$H NMR (300 MHz, $CDCl_3$, TMS): δ 7.62 (m, 2H), 7.31 (m, 3H), 7.09 (m, 2H) 2.63 (s, 1H) 2.30 (s, 1H), 1.02 (s, 9H).

$^{13}$C NMR (75 MHz, $CDCl_3$): δ 141.64, 127.583, 127.49, 127.10, 86.80, 78.88, 73.99, 39.27, 25.31.

Step 3: $(PPh_3)_2Cl_2Ru$(3-t-butyl-indene) (3C)

$(PPh_3)_3RuCl_2$ (1 eq., 0.575 g, 0.6 mmol) and 1-t-butyl-1-phenyl-prop-2-yn-1-ol (compound B, 1.5 eq., 0.17 g, 0.9 mmol) were added in 4 ml HCl/dioxane solution (0.15 mol/1). The solution was heated to 90° C. for 3 hour, after which the solvent was removed under vacuum. Hexane (20 ml) was added to the flask and the solid was ultrasonically removed from the wall. The resulting suspension was filtered and washed two times using hexane (5 ml). The remaining solvent was evaporated affording a red-brown powder; 0.48 g (Yield: 92%). The product was characterized by NMR spectra $^{31}$P.

$^{31}$P NMR (121.49 MHz, $CDCl_3$): δ 28.76.

Example 4: Synthesis of $(PPh_3)_2Cl_2Ru$(3-naphtyl-inden-1-ylidene)

Scheme 4: Synthesis of $(PPh_3)_2Cl_2Ru$(3-naphtyl-inden-1-ylidene) (4C)

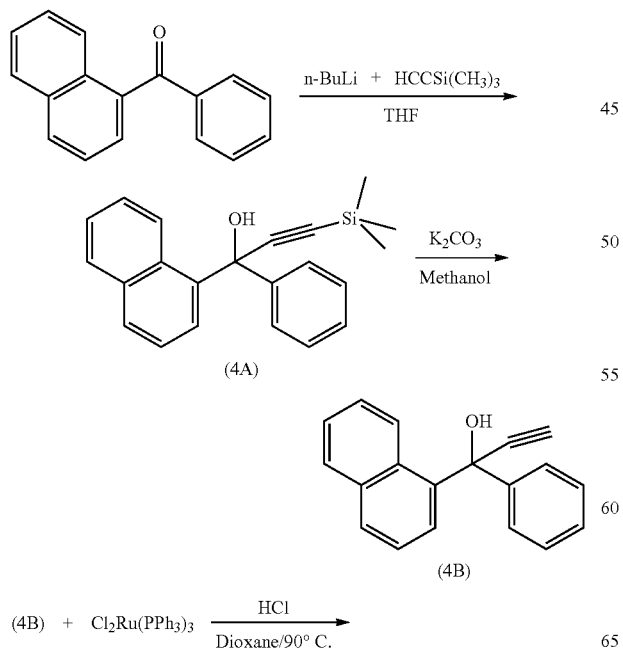

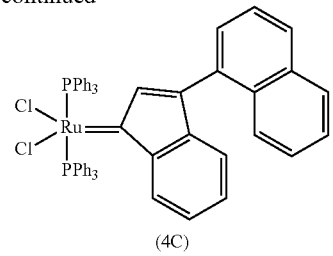

(4C)

Step 1: 1-naphtyl-1-phenyl-3-(trimethylsilyl)prop-2-yn-1-ol (4A)

n-BuLi (2.5 M in hexane) (1.3 eq., 1.90 ml, 4.76 mmol,) was added drop wise to a cold solution (−90° C.) of trimethylsilylacetylene (1.3 eq., 0.68 ml, 4.76 mmol) in anhydrous THF (7 ml) under an argon atmosphere. After addition, the resulting solution was stirred for another 5 min in a cold bath and 30 minutes at room temperature. Thereafter, 1-naphthyl-1-phenyl methanone (1.0 eq. 0.85 g, 3.66 mmol) in 7 ml dry THF was added slowly to the trimethylsilylacetylene solution at −90° C. and the resulting mixture was allowed to heat up and refluxed for 3 hours. The crude reaction mixture was quenched using 5 ml 1N HCl and diluted with diethyl ether. The organic phase was washed with water and the aqueous phase was extracted twice with diethyl ether, thereafter the ether fractions were combined and dried on anhydrous $MgSO_4$. After removal of $MgSO_4$ by filtration, and evaporation of the solvent an oily liquid was obtained in quantitative yield. The obtained product was used without further purification.

Step 2: 1-naphtyl-1-phenyl-prop-2-yn-1-ol (4B)

A solution 1-naphtyl-1-phenyl-3-(trimethylsilyl)prop-2-yn-1-ol (obtained from previous step) and $K_2CO_3$ (1 eq., 0.5 g, 3.58 mmol) in dry methanol (5 ml) was stirred at room temperature for 3 h. Subsequently, methanol was removed followed by addition of 40 ml diethyl ether and 10 ml water. Afterwards the crude reaction mixture was quenched using 15 ml 1N HCl and diluted with diethyl ether. The organic phase was separated and washed with water; the aqueous phases were combined and extracted three times with 20 ml diethyl ether. Subsequently the organic fractions were combined and dried on $MgSO_4$. Removal of $MgSO_4$ by filtration, and column chromatography (silica gel, Hexane/EtOAc=30:1), the solvent was evaporated yielding a white sticky material (0.8 g, yield 84.7% for step 1+2).

$^1$H NMR (300 MHz, $CDCl_3$, TMS): δ 8.13 (dd, 1H), 8.07 (d, 1H), 7.85 (t, 2H), 7.56-7.59 (m, 2H), 7.52 (t, 1H), 7.39 (td, 1H), 7.28-7.39 (m, 4H), 2.94 (s, 1H), 2.92 (s, 1H).

$^{13}$C NMR (75 MHz, $CDCl_3$): δ 144.11, 138.11, 134.65, 129.88, 129.67, 128.68, 128.56, 128.15, 126.75, 126.33, 125.50, 125.40, 124.80, 124.73, 86.19, 76.72, 74.45.

Step 3: $(PPh_3)_2Cl_2Ru$(3-naphtyl-inden-1-ylidene) (4C)

$(PPh_3)_3RuCl_2$ (1 eq., 0.575 g, 0.6 mmol) and 1-naphtyl-1-phenyl-prop-2-yn-1-ol (compound B, 1.5 eq., 0.23 g, 0.9 mmol) were added in 4 ml HCl/dioxane solution (0.15 mol/l). The solution was heated to 90° C. for 3 hour, after which the solvent was removed under vacuum. Hexane (20 ml) was added to the flask and the solid was ultrasonically removed from the wall. The resulting suspension was filtered and washed two times using hexane (5 ml). The remaining solvent was evaporated affording a red-brown powder; 0.51 g (Yield: 90%). The product was characterized by NMR spectra $^{31}$P.

$^{31}$P NMR (121.49 MHz, CDCl$_3$): δ 28.75.

Example 5: Synthesis of (PPh$_3$)$_2$Cl$_2$Ru(3-c-hexyl-inden-1-ylidene)

Scheme 5: Synthesis of (PPh$_3$)$_2$Cl$_2$Ru(3-c-hexyl-inden-1-ylidene) (5B)

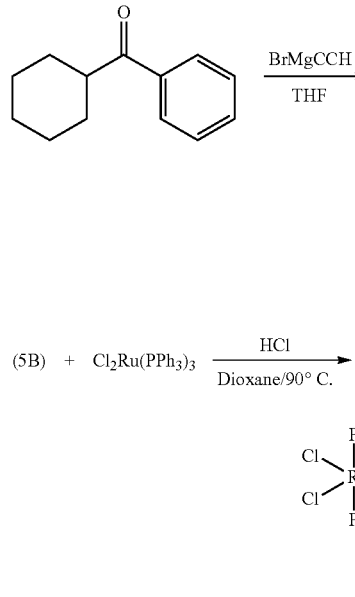

Step 1: 1-c-hexyl-1-phenyl-prop-2-yn-1-ol (5A)

Ethynylmagnesium bromide (1.2 eq, 12.7 mmol, 25.4 ml) (0.5M in THF) was added to cyclo-hexyl(phenyl)methanone (1 eq., 10.6 mmol, 2 g) in dry THF (7 ml). The resulting solution was allowed to heat up under reflux overnight. The crude mixture was quenched by addition of 1N HCl (15 ml) and diluted with diethyl ether. The organic layer was separated; the aqueous layer was extracted twice with diethyl ether. The organic layers were combined dried on anhydrous MgSO$_4$, filtered, and concentrated under vacuum. The product obtained after column chromatography (Hexane: EtOAc 9:1) is a yellow liquid 2.01 g yield 88.6%.

$^1$H NMR (300 MHz, CDCl$_3$): 1.03-1.28 (m, 5H), 1.48 (d, 1H), 1.61-1.79 (m, 4H), 1.95 (m, 1H), 2.37 (s, 1H), 2.67 (s, 1H), 7.33 (m, 3H), 7.60 (dd, 2H).

$^{13}$C NMR (100 MHz, CDCl$_3$): δ 26.17, 26.23, 27.29, 27.74, 49.8, 74.83, 76.56, 85.52, 126.14, 127.69, 127.9, 143.33.

Step 2: (PPh$_3$)$_2$Cl$_2$Ru(3-c-hexyl-indene-1-ylidene) (5B)

(PPh$_3$)$_3$RuCl$_2$ (1 eq., 0.575 g, 0.6 mmol) and 1-c-hexyl-1-phenyl-prop-2-yn-1-ol (compound E, 1.5 eq., 0.19 g, 0.9 mmol) were added in 4 ml HCl/dioxane solution (0.15 mol/l). The solution was heated to 90° C. for 3 hour, after which the solvent was removed under vacuum. Hexane (20 ml) was added to the flask and the solid was ultrasonically removed from the wall. The resulting suspension was filtered and washed two times using hexane (5 ml). The remaining solvent was evaporated affording a red-brown powder; 0.51 g (Yield: 95%). The product was characterized by NMR spectra $^{31}$P.

$^{31}$P NMR (121.49 MHz, CDCl$_3$): δ 29.64.

Example 6: Synthesis of (PPh$_3$)$_2$Cl$_2$Ru(3-2,6-dimethylphenyl-inden-1-ylidene)

Scheme 6: Synthesis of (PPh$_3$)$_2$Cl$_2$Ru(3-2,6-dimethylphenyl-inden-1-ylidene) (6E)

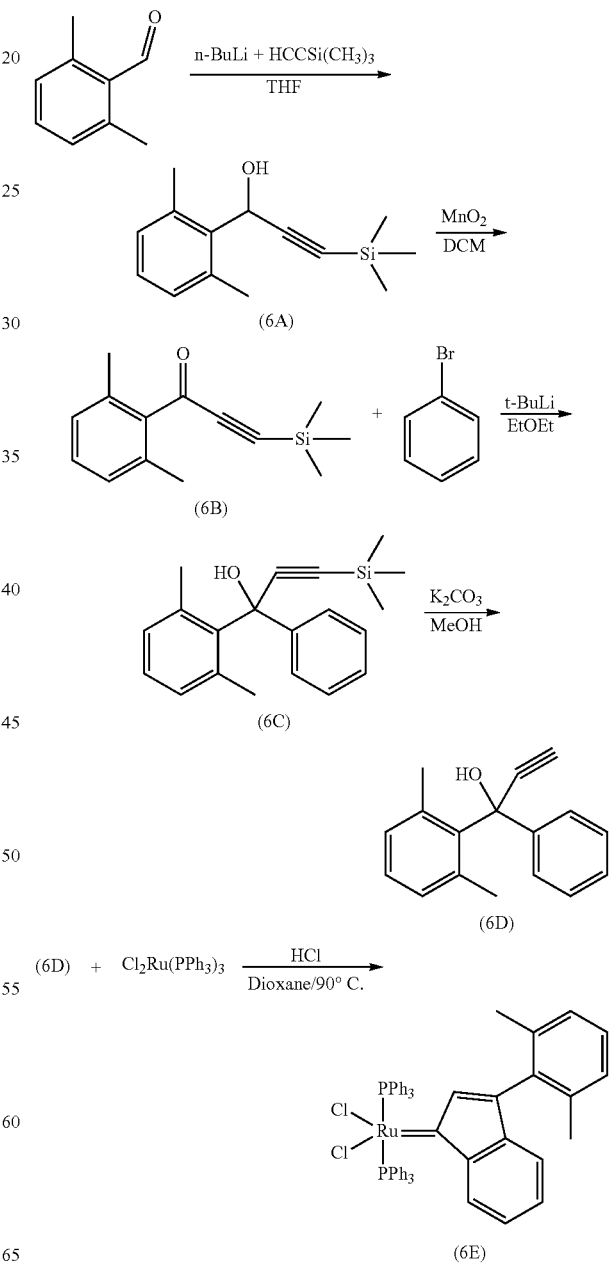

Step 1: 1-2,6-dimethylphenyl 3-(trimethylsilyl)prop-2-yn-1-ol (6A)

n-BuLi (2.5 M in hexane) (1.5 eq., 16.2 mmol, 6.5 ml) was added to a solution of trimethylsilyl acetylene (1.5 eq., 16.2 mmol, 2.3 ml) in 45 ml of dry THF at −90° C. After addition, the reaction mixture was warmed up till room temperature and stirred for 30 min. 2,6-dimethylbenzaldehyde (1 eq., 1.46 g, 10.8 mmol) in dry THF (10 ml) was added and the resulting mixture was stirred for 1 h at −90° C. and allowed to warm up to room temperature for 20 h. The crude mixture was quenched using 20 ml 1N HCl and diluted with diethyl ether. The organic phase was washed with water and the aqueous phase was extracted twice with diethyl ether, thereafter the ether fractions were combined and dried with anhydrous $MgSO_4$. Removal of $MgSO_4$ by filtration followed by purification, using flash column chromatography (silica gel, n-Hexane/EtOAc=15/1) a yellow oil was obtained; 2.34 g (yield: 93.3%).

$^1$H NMR (300 MHz, $CDCl_3$, TMS): δ 7.11 (t, 1H), 7.03 (d, 2H), 5.90 (s, 1H), 2.53 (s, 6H), 0.17 (tetra, 9H);

$^{13}$C NMR (75 MHz, $CDCl_3$): δ137.01, 136.35, 129.42, 128.36, 104.94, 91.09, 61.10, 20.61, 0.00.

Step 2: 1-2,6-dimethylphenyl-3-(trimethylsilyl)prop-2-yn-1-one (6B)

A solution of sodium dichromate dihydrate (1 eq., 2.88 g, 9.6 mmol) and concentrated sulphuric acid (2 eq., 1.04 ml, 19.2 mmol) in glacial acetic acid (20 ml) was added drop wise to a solution of 1-(2,6-dimethylphenyl)-3-(trimethylsilyl)prop-2-yn-1-ol (1 eq., 2.24 g, 9.6 mmol) in glacial acetic acid (20 ml) at 0° C. The mixture was stirred at room temperature for 1 h., thereafter the excess oxidant was decomposed by the addition of 2-propanol (3 ml). After 10 min., a saturated NaCl solution (50 ml) was added and the mixture was extracted with $CH_2Cl_2$ (2×30 ml). The organic fractions were combined, washed with a 5% $NaHCO_3$ solution (24 ml) and finally washed with a saturated NaCl solution (24 ml). The organic phase was separated and dried over anhydrous $MgSO_4$, filtered and evaporated. The crude product thus obtained was purified by flash chromatography using Hexane:EtOAc (30:1) as the mobile phase yielding the desired product, a yellow liquid (2.1 g, yield: 92.2%).

$^1$H NMR (300 MHz, $CDCl_3$, TMS): δ 7.20 (t, 1H), 7.04 (d, 2H), 2.37 (s, 6H), 0.24 (s, 9H).

$^{13}$C NMR (75 MHz, $CDCl_3$): δ 184.96, 140.57, 135.83, 130.58, 129.07, 103.96, 101.93, 20.56, 0.00.

Step 3: 1,1-2,6-dimethylphenyl phenyl 3-(trimethylsilyl)prop-2-yn-1-ol (6C)

t-BuLi (2.5 M in hexane) (2 eq, 7.9 ml, 15 mmol) was added drop wise to a solution of bromobenzene (1 eq., 0.78 g, 7.5 mmol) in 50 ml of dry diethyl ether at −90° C. under inert atmosphere. The resulting solution was stirred for another 30 minutes at room temperature before slowly adding 1-(2,6-dimethylphenyl)-3-(trimethylsilyl)prop-2-yn-1-one (1.1 eq., 1.9 g, 8.25 mmol) dissolved in dry diethyl ether. The resulting mixture was stirred overnight at room temperature and then quenched using 10 ml of a saturated $NH_4Cl$ and diluted with diethyl ether. The organic phase was washed with water and the aqueous phase were combined and extracted twice with ether, thereafter the ether fractions were combined and dried on anhydrous $MgSO_4$. After removal of $MgSO_4$ by filtration, and evaporation of the solvent an oily liquid was obtained in quantitative yield

Step 4: 1-2,6-dimethylphenyl-1-phenyl-prop-2-yn-1-ol (6D)

A solution 1-2,6-dimethylphenyl-1-phenyl-prop-2-yn-1-ol (obtained from previous step) and $K_2CO_3$ (1 eq., 1 g, 7.5 mmol) in dry methanol (8 ml) was stirred at room temperature for 3 h. Subsequently, methanol was removed followed by addition of 20 ml diethyl ether and 10 ml water, diluted with diethyl ether (20 ml) and washed with 1N HCl 15 ml. The organic layer was separated and the aqueous layer was extracted twice with diethyl ether. Subsequently the organic fractions were combined and dried on $MgSO_4$. Removal of $MgSO_4$ by filtration, column chromatography (silica gel, Hexane/EtOAc=60/1) and solvent evaporation afforded 1-(2,6-dimethylphenyl)-1-phenyl-prop-2-yn-1-ol (1.42 g, yield 80%).

$^1$H NMR (300 MHz, $CDCl_3$): δ 7.52 (d, 2H), 7.28-7.35 (m, 3H), 7.09 (t, 1H), 7.00 (d, 2H), 2.85 (s, 1H), 2.53 (m, 1H), 2.36 (s, 6H).

$^{13}$C NMR (75 MHz, $CDCl_3$): δ 144.87, 139.08, 137.04, 130.79, 128.59, 128.08, 127.27, 126.25, 86.12, 76.65, 75.69, 24.09.

ESI [M-OH]: 219.1, calculated: 219.1.

Step 5: $(PPh_3)_2Cl_2Ru(3$-2,6-dimethylphenyl-inden-1-ylidene (6E)

$(PPh_3)_3RuCl_2$ (1 eq., 0.575 g, 0.6 mmol) and 1-2,6-dimethylphenyl-1-phenyl-prop-2-yn-1-ol (compound D, 1.5 eq., 0.213 g, 0.9 mmol) were added in 4 ml HCl/dioxane solution (0.15 mol/l). The solution was heated to 90° C. for 3 hour, after which the solvent was removed under vacuum. Hexane (20 ml) was added to the flask and the solid was ultrasonically removed from the wall. The resulting suspension was filtered and washed two times using hexane (5 ml). The remaining solvent was evaporated affording a red-brown powder; 0.50 g (Yield: 90%). The product was characterized by NMR spectra $^{31}$P.

$^{31}$P NMR (121.49 MHz, $CDCl_3$): δ 29.64.

Example 7: Synthesis of $(PPh_3)Cl_2Ru(3$-t-Butyl-5,6-methoxy-8-methoxymethylene)-inden-1-ylidene Scheme 7: Synthesis of $(PPh_3)_2Cl_2Ru(3$-t-Butyl-5,6-methoxy-8-methoxymethylene)-inden-1-ylidene (7F)

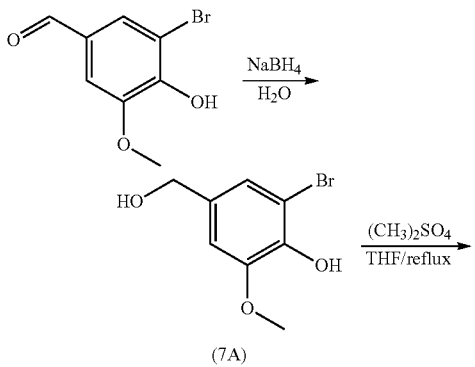

(7A)

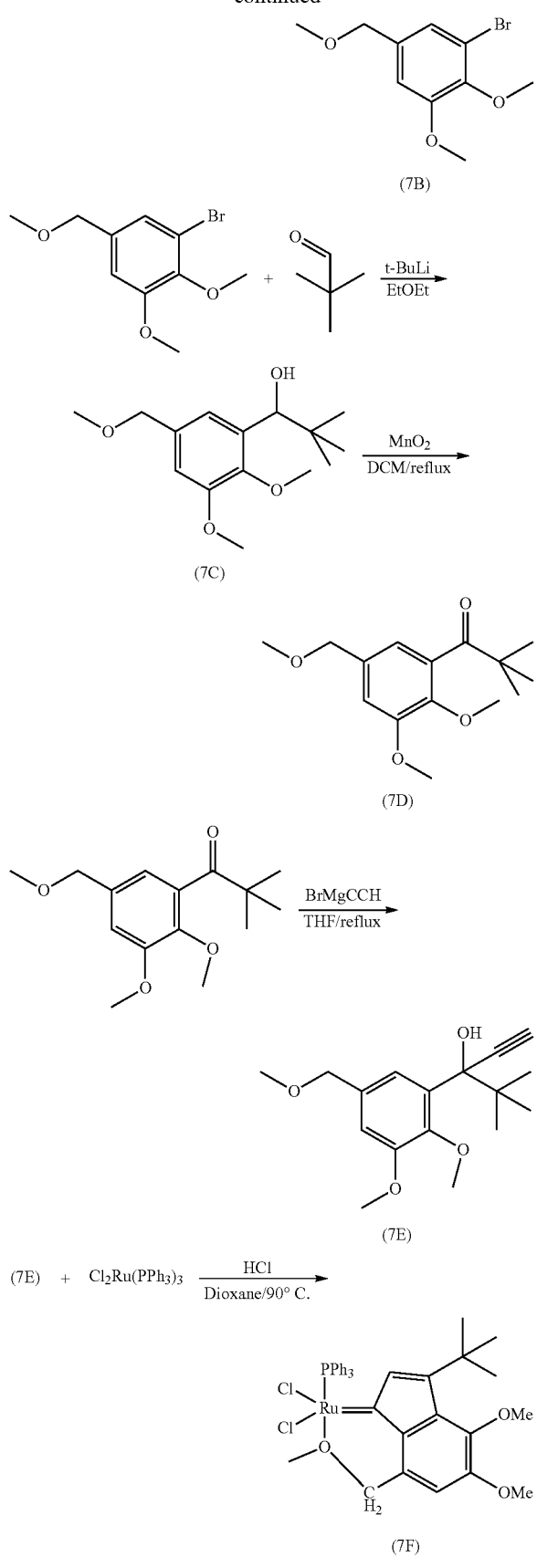

Step 1:
2-bromo-4-(hydroxymethyl)-6-methoxyphenol (7A)

5-Bromovanillin (1 eq., 5 g, 21.8 mmol) was added to a solution of NaOH (1.5 eq., 1.3 g, 32.7 mmol) in water (80 ml) followed by the addition of a $NaBH_4$ (1.1 eq., 0.9 g, 24 mmol) water solution at 0° C. The reaction was vigorously stirred for 1 hour at 0° C. and at room temperature for another 2 hours. After completion (monitored by TLC) the solution was acidified to pH 2 using 6 N HCl and 400 ml ethylacetate (EtOAc) was added. Thereafter, the EtOAc fraction was separated, washed two times with water and dried on $Na_2SO_4$. Removal of $Na_2SO_4$ by filtration, the filtrate was concentrated affording 4.7 g of a white solid (Yield: 92.9%).

$^1$H NMR (300 MHz, DMSO-$d_6$): δ 9.23 (s, 1H), 7.00 (s, 1H), 6.90 (s, 1H), 5.13 (t, 1H), 4.38 (d, 2H), 3.80 (s, 3H);
$^{13}$C NMR (75 MHz, DMSO-$d_6$): δ 148.22, 142.26, 134.57, 122.01, 109.57, 108.86, 62.20, 56.02.

Step 2:
1-bromo-2,3-dimethoxy-5-(methoxymethyl)benzene (7B)

Dimethyl sulfate (3 eq., 3.3 g, 25.9 mmol) was added to a solution of 2-bromo-4-(hydroxymethyl)-6-methoxyphenol (1 eq., 2 g, 8.6 mmol) and KOH (4 eq., 1.9 g, 34.5 mmol) in THF (16 ml) at room temperature. After addition, the solution was refluxed for 3 h and followed by 12 h at 60° C. Thereafter, 35 ml of 1 N HCl and 40 ml diethyl ether were added. After separation of the organic phase, the aqueous phase was extracted 3 times with 10 ml diethyl ether. The organic fractions were combined and dried on $MgSO_4$. Removal of $MgSO_4$ by filtration, the filtrate was concentrated affording 2.23 g of a colorless oil (Yield: 99.5%).

$^1$H NMR (300 MHz, $CDCl_3$, TMS): δ 7.10 (dt, 1H), 6.86 (d, 1H), 4.37 (s, 2H), 3.88 (s, 3H), 3.84 (s, 3H), 3.39 (s, 3H);
$^{13}$C NMR (75 MHz, $CDCl_3$): δ 153.76, 145.87, 135.42, 123.79, 117.46, 110.89, 73.84, 60.58, 58.24, 56.08.

Step 3: 1-(2,3-dimethoxy-5-(methoxymethyl)phenyl)-2,2-dimethylpropan-1-ol (7C)

t-BuLi (2.5 M in hexane) (1.5 eq., 9.2 ml, 17.4 mmol) was added to a solution of 1-bromo-2,3-dimethoxy-5-(methoxymethyl)benzene (1 eq., 3.02 g, 11.6 mmol) in 20 ml of dry diethyl ether at −90° C. The reaction mixture was warmed up till room temperature and stirred for 30 min. Cooling the mixture to −90° C., pivalaldehyde (1.5 eq., 1.5 g, 17.4 mmol) was added and stirred for 1 h. Allowing the mixture to warm up to room temperature, the mixture was further stirred for 12 h. and quenched using 1N HCl (20 ml). After addition of diethyl ether, the organic layer was separated from the water layer. The latter was extracted twice with diethyl ether, all organic layers were combined and dried using anhydrous $MgSO_4$. Removal of $MgSO_4$ by filtration followed by purification using flash column chromatography (silica gel, Hexane/ethyl acetate=20:1) and finally evaporation of the solvent affording a white solid 2.63 g (Yield: 84.5%).

$^1$H NMR (300 MHz, $CDCl_3$, TMS): δ 6.90 (d, 1H), 6.86 (d, 1H), 4.75 (s, 1H), 4.40 (s, 2H), 3.87 (s, 3H), 3.83 (s, 3H), 3.39 (s, 3H), 2.29 (b, 1H);
$^{13}$C NMR (75 MHz, $CDCl_3$): δ 152.25, 146.33, 134.92, 133.05, 120.01, 110.51, 76.69, 74.78, 60.64, 58.09, 55.70, 36.47, 26.01.

Step 4: 1-(2,3-dimethoxy-5-(methoxymethyl)phenyl)-2,2-dimethylpropan-1-one (7D)

A solution of 1-(2,3-dimethoxy-5-(methoxymethyl)phenyl)-2,2-dimethylpropan-1-ol (1 eq., 2.16 g, 8.1 mmol) and MnO$_2$ (10 eq., 7.0 g, 81 mmol) in dry CH$_2$Cl$_2$ (60 ml) was brought to reflux. After completion of the reaction (monitored by TLC) MnO$_2$ was filtered off using a pad of cilite. Evaporation of the solvent afforded a yellowish product in quantitative yield. The obtained product was used without further purification.

$^1$H NMR (300 MHz, CDCl$_3$, TMS): 6.93 (d, 1H), 6.59 (d, 1H), 4.39 (s, 2H), 3.89 (s, 3H), 3.77 (s, 3H), 3.39 (s, 3H), 1.21 (s, 9H).

Step 5: 3-(2,3-dimethoxy-5-(methoxymethyl)phenyl)-4,4-dimethylpent-1-yn-3-ol (7E)

Ethynylmagnesium bromide (0.5 M in THF) (1.2 eq., 19.4 ml, 9.7 mmol) was added to 1-(2,3-dimethoxy-5-(methoxymethyl)phenyl)-2,2-dimethylpropan-1-one (1 eq., 2.15 g, 8.1 mmol) in dry THF (11 ml). The resulting solution was allowed to heat up under reflux overnight. The crude mixture was quenched by addition of 1N HCl (10 ml) and diluted with diethyl ether. The organic layer was separated; the aqueous layer was extracted twice with diethyl ether. The organic layers were combined dried on anhydrous MgSO$_4$, filtered, and concentrated under vacuum. The product obtained after column chromatography (Hexane/EtOAc=15:1) is a yellow liquid 1.99 g (Yield: 84%).

$^1$H NMR (300 MHz, CDCl$_3$, TMS): 7.15 (d, 1H), 6.91 (d, 1H), 5.31 (bs, 1H) 4.41 (s, 2H), 3.93 (s, 3H), 3.88 (s, 3H), 3.38 (s, 3H), 2.63 (s, 1H), 1.03 (s, 9H).

Step 6: (PPh$_3$)Cl$_2$Ru(3-t-Butyl-5,6,7-methoxy-8-(CH$_2$—O-Me)-inden-1-ylidene) (7F)

(PPh$_3$)$_3$RuCl$_2$ (1 eq., 0.575 g, 0.6 mmol) and 3-(2,3-dimethoxy-5-(methoxymethyl)phenyl)-4,4-dimethylpent-1-yn-3-ol (1.5 eq., 0.263 g, 0.9 mmol) were added in 4 ml HCl/dioxane solution (0.15 mol/l). The solution was heated to 90° C. for 3 hour, after which the solvent was removed under vacuum. Hexane (20 ml) was added to the flask and the solid was ultrasonically removed from the wall. The resulting suspension was filtered and washed two times using hexane (5 ml). The remaining solvent was evaporated affording a orange powder; 0.31 g (Yield: 80%). The product was characterized by NMR spectra $^{31}$P.

$^{31}$P NMR (121.49 MHz, CDCl$_3$): δ 52.09.

Example 8: Synthesis of (PCy$_3$)$_2$Cl$_2$Ru(3-2-methylphenyl-5-methyl-inden-1-ylidene)

Scheme 8: Synthesis of (PCy$_3$)$_2$Cl$_2$Ru(3-2-methylphenyl-5-methyl-inden-1-ylidene) (8)

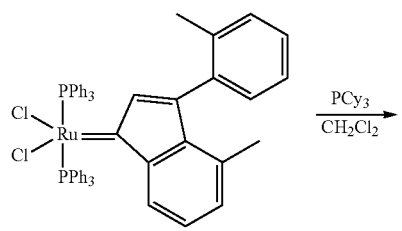

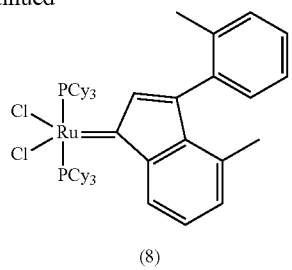

(8)

A 25 ml vial was charged with (PPh$_3$)$_2$Cl$_2$Ru(3-2-methylphenyl-5-methyl-inden-1-ylidene) (1 eq., 0.4574 g, 0.5 mmol), tricyclohexylphosphine (3 eq., 0.42 g, 1.5 mmol) and dichloromethane (10 ml). After completion of the reaction (1 h) the resulting slurry was dried under vacuum and 20 ml isopropanol was added. Filtration afforded a redbrown powder, which after washing with 5 ml isopropanol (2×) and drying under vacuum afforded 0.44 g of catalyst (Yield: 93%). The product was characterized by NMR spectra $^1$H and $^{31}$P.

$^1$H NMR (300 MHz, CDCl$_3$, TMS): δ 8.54 (d, 1H), 7.24-7.29 (m, 1H), 7.10-7.17 (m, 4H), 7.07 (s, 1H), 7.02 (d, 1H), 2.61 (d, 6H), 2.22 (s, 3H), 1.18-1.96 (m, 63H).

$^{31}$P NMR (121.49 MHz, CDCl$_3$): δ 31.75, 31.56.

Characteristic values of $^1$H and $^{31}$P: H—C8: 8.54 ppm (d, 1H) and P: 31.75 and 31.56 ppm.

Example 9: Synthesis of (PCy$_3$)$_2$Cl$_2$Ru(3-2-methoxyphenyl-5-methoxyphenyl-inden-1-ylidene)

Scheme 9: Synthesis of (PCy$_3$)$_2$Cl$_2$Ru(3-2-methoxyphenyl-5-methoxyphenyl-inden-1-ylidene) (9)

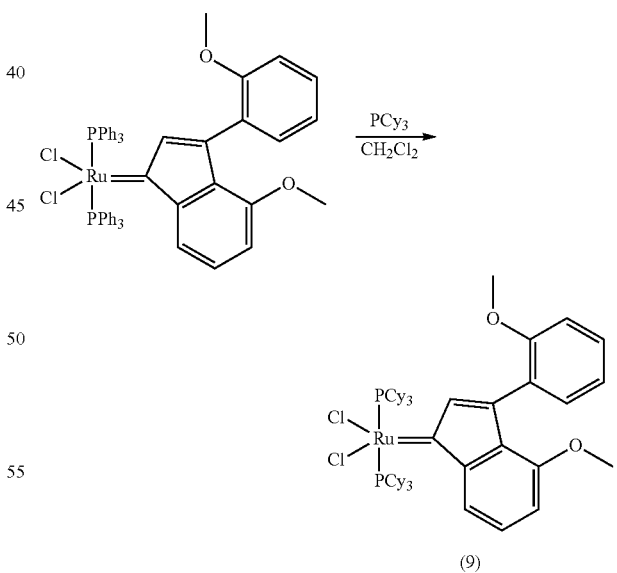

(9)

A 25 ml vial was charged with (PPh$_3$)$_2$Cl$_2$Ru(3-2-methoxyphenyl-5-methoxyphenyl-inden-1-ylidene) (1 eq., 0.4734 g, 0.5 mmol), tricyclohexylphosphine (3 eq., 0.42 g, 1.5 mmol) and dichloromethane (10 ml). After completion of the reaction (1 h) the resulting slurry was dried under vacuum and 20 ml isopropanol was added. Filtration afforded a red brown powder, which after washing with 5 ml isopropanol (2x) and drying under vacuum afforded 0.44 g of catalyst (Yield: 89%). The product was characterized by NMR spectra ¹H and ³¹P.

Characteristic values of ¹H and ³¹P: H—C8: 8.32 ppm (d, 1H) and P: 30.56 ppm.

Example 10: Synthesis of (PCy₃)₂Cl₂Ru(3-t-butyl-inden-1-ylidene)

Scheme 10: Synthesis of (PCy₃)₂Cl₂Ru(3-t-butyl-inden-1-ylidene) (10)

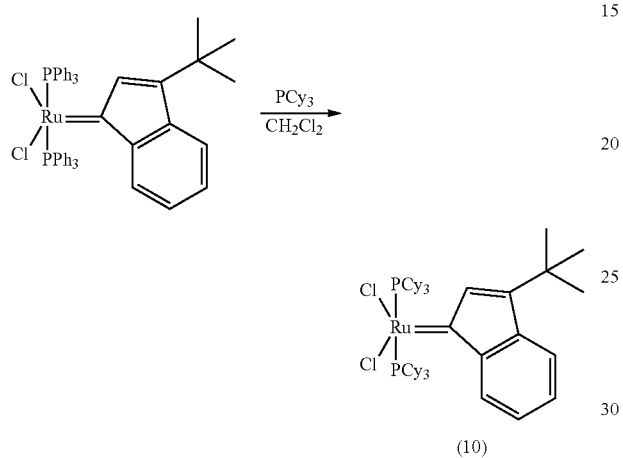

(10)

A 25 ml vial was charged with (PPh₃)₂Cl₂Ru(3-t-butyl-inden-1-ylidene) (1 eq., 0.4334 g, 0.5 mmol), tricyclohexylphosphine (3 eq., 0.42 g, 1.5 mmol) and dichloromethane (10 ml). After completion of the reaction (1 h) the resulting slurry was dried under vacuum and 20 ml isopropanol was added. Filtration afforded a redbrown powder, which after washing with 5 ml isopropanol (2x) and drying under vacuum afforded 0.41 g of catalyst (Yield: 90%). The product was characterized by NMR spectra ¹H and ³¹P.

Characteristic values of ¹H and ³¹P: H—C8: 8.60 ppm (d, 1H) and P: 31.29 ppm.

Example 11: Synthesis of (PCy₃)₂Cl₂Ru(3-naphtyl-inden-1-ylidene)

Scheme 11: Synthesis of (PCy₃)₂Cl₂Ru(3-naphtyl-inden-1-ylidene) (11)

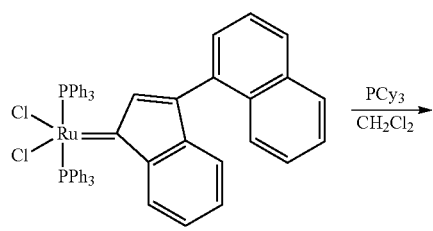

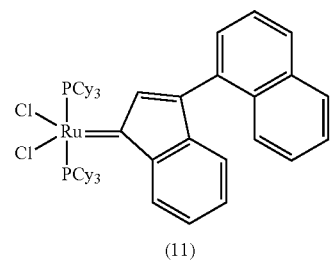

(11)

A 25 ml vial was charged with (PPh₃)₂Cl₂Ru(3-naphtyl-inden-1-ylidene) (1 eq., 0.4684 g, 0.5 mmol), tricyclohexylphosphine (3 eq., 0.42 g, 1.5 mmol) and dichloromethane (10 ml). After completion of the reaction (1 h) the resulting slurry was dried under vacuum and 20 ml isopropanol was added. Filtration afforded a red brown powder, which after washing with 5 ml isopropanol (2x) and drying under vacuum afforded 0.43 g of catalyst (Yield: 88%). The product was characterized by NMR spectra ¹H and ³¹P.

Characteristic values of ¹H and ³¹P: H—C8: 8.71 ppm (d, 1H) and P: 32.06 ppm.

Example 12: Synthesis of (PCy₃)₂Cl₂Ru(3-c-hexyl-inden-1-ylidene)

Scheme 12: Synthesis of (PCy₃)₂Cl₂Ru(3-c-hexyl-inden-1-ylidene) (12)

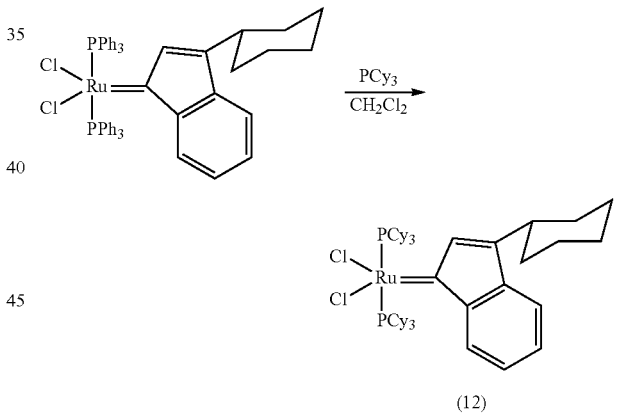

(12)

A 25 ml vial was charged with (PPh₃)₂Cl₂Ru(3-c-hexyl-inden-1-ylidene) (1 eq., 0.4464 g, 0.5 mmol), tricyclohexylphosphine (3 eq., 0.42 g, 1.5 mmol) and dichloromethane (10 ml). After completion of the reaction (1 h) the resulting slurry was dried under vacuum and 20 ml isopropanol was added. Filtration afforded a red brown powder, which after washing with 5 ml isopropanol (2x) and drying under vacuum afforded 0.42 g of catalyst (Yield: 90%). The product was characterized by NMR spectra ¹H and ³¹P.

Characteristic values of ¹H and ³¹P: H—C8: 8.50 ppm (d, 1H) and P: 31.40 ppm.

Example 13: Synthesis of (PCy₃)₂Cl₂Ru(3-2,6-dimethylphenyl-inden-1-ylidene)

Scheme 13: Synthesis of (PCy₃)₂Cl₂Ru(3-2,6-dimethylphenyl-inden-1-ylidene) (13)

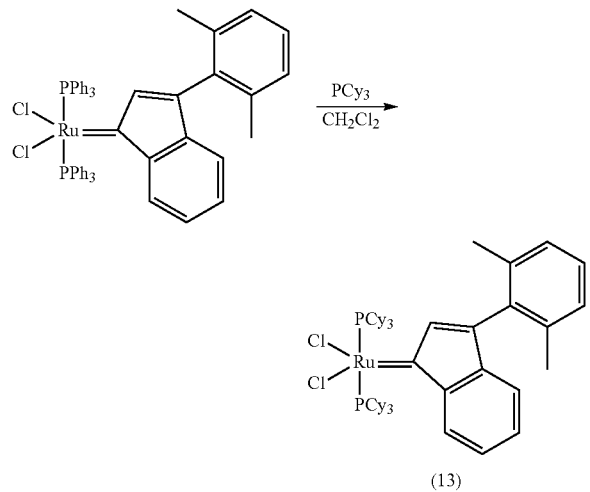

(13)

A 25 ml vial was charged with (PPh₃)₂Cl₂Ru(3-2,6-dimethylphenyl-inden-1-ylidene) (1 eq., 0.4574 g, 0.5 mmol), tricyclohexylphosphine (3 eq., 0.42 g, 1.5 mmol) and dichloromethane (10 ml). After completion of the reaction (1 h) the resulting slurry was dried under vacuum and 20 ml isopropanol was added. Filtration afforded a red brown powder, which after washing with 5 ml isopropanol (2×) and drying under vacuum afforded 0.43 g of catalyst (Yield: 88%). The product was characterized by NMR spectra ¹H and ³¹P.

Characteristic values of ¹H and ³¹P: H—C8: 8.71 ppm (d, 1H) and P: 32.93 ppm.

Example 14: Synthesis of (S-IMes)(PCy₃)Cl₂Ru(3-2-methylphenyl-5-methyl-inden-1-ylidene)

Scheme 14: Synthesis of (S-IMes)(PCy₃)Cl₂Ru(3-2-methylphenyl-5-methyl-inden-1-ylidene) (14)

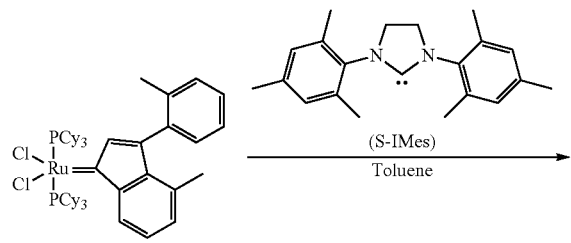

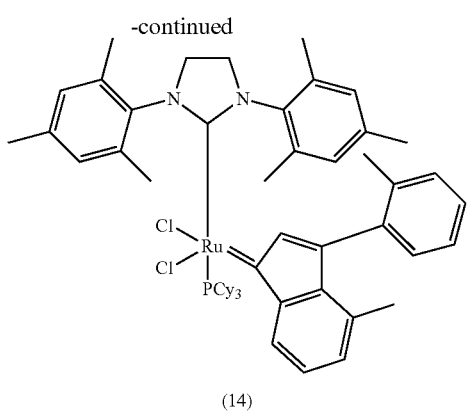

(14)

S-IMes=saturated 1,3-bis(mesityl)-imidazolidine-2-ylidene (1,3-Bis(2,4,6-trimethylphenyl)-2-imidazolidinylidene)

A 10 mL vial was charged with (PCy₃)₂Cl₂Ru(3-2-methylphenyl-5-methyl-inden-1-ylidene) (1 eq., 0.3804 g, 0.4 mmol) and S-IMes (1.1 eq., 0.134 g, 0.44 mmol). Dry toluene (3 ml) was added under inert atmosphere. The mixture was vigorously stirred at 50° C. for 30 minutes and dried under vacuum followed by addition of 10 ml isopropanol. After filtration and washing (two times 5 ml isopropanol), an orange powder was obtained; 0.33 g (Yield: 84%). The product was characterized by NMR spectra ¹H, ¹³C, and ³¹P.

¹H NMR (300 MHz, CDCl₃, TMS): δ 8.47 (d, 1H), 7.44 (dd, 1H), 7.20-7.28 (m, 2H), 7.04-7.11 (m, 3H), 6.99 (d, 1H), 6.93 (s, 1H), 6.88 (d, 1H), 6.81 (s, 1H), 6.05 (s, 1H), 3.70-4.07 (m, 4H), 2.74 (s, 3H), 2.68 (s, 3H), 2.38 (s, 3H), 2.33 (s, 3H), 2.14 (s, 3H), 2.02 (s, 3H), 1.87 (s, 3H), 0.86-1.83 (m, 36H).

¹³C NMR (75 MHz, CDCl₃): δ 294.06, 293.96, 217.16, 216.19, 143.91, 140.11, 139.79, 139.52, 139.39, 138.77, 138.29, 136.94, 136.85, 136.27, 135.69, 134.04, 130.70, 130.01, 129.88, 129.57, 128.94, 128.58, 128.14, 127.25, 127.13, 126.27, 125.30, 125.05, 52.68, 52.64, 52.29, 52.26, 33.09, 32.87, 29.47, 29.24, 27.70, 27.57, 26.20, 21.18, 20.91, 20.32, 20.15, 19.36, 18.97, 18.92, 18.44.

³¹P NMR (121.49 MHz, CDCl₃): δ 26.75.

Example 15: Synthesis of (S-IMes)(Pyridine)Cl₂Ru (3-2-methylphenyl-5-methyl-inden-1-ylidene)

Scheme 15: Synthesis of (S-IMes)(Pyridine)Cl₂Ru(3-2-methylphenyl-5-methyl-inden-1-ylidene) (15)

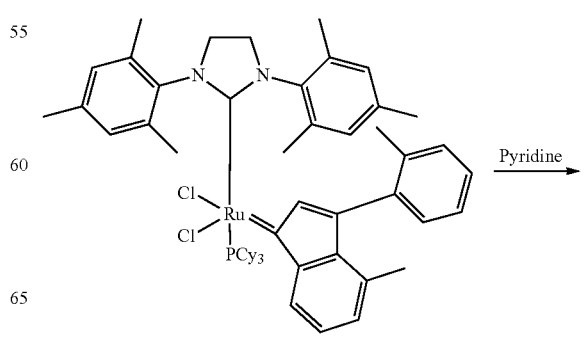

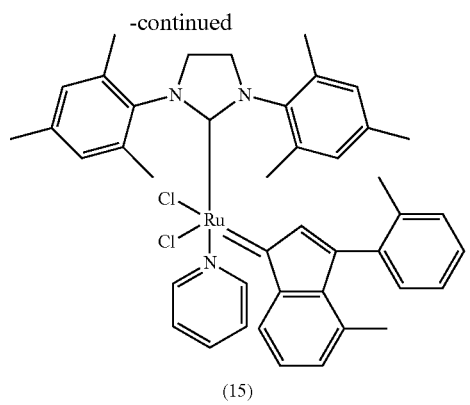

(15)

(S-IMes)(PCy₃)Cl₂Ru(3-2-methylphenyl-5-methyl-inden-1-ylidene) (1 eq., 0.25 g, 0.256 mmol) was dissolved in pyridine (0.21 ml) and stirred at room temperature for 24 hours. An orange brown precipitate is formed upon addition of n-hexane (10 ml) and subsequent cooling to −40° C. Filtration of the precipitate, washing with 3 times n-hexane (5 ml each) and drying in vacuo afforded 0.14 g (Yield: 70%) of an orange powder. The product was characterized by NMR spectra $^1$H.

$^1$H NMR (300 MHz, CDCl₃, TMS): δ 8.21 (d, 1H), 7.89 (d, 2H), 6.80-7.47 (m, 13H), 6.29 (s, 1H), 4.24 (m, 2H), 3.99 (m, 2H), 2.79 (s, 3H), 2.68 (s, 3H), 2.37 (s, 3H), 2.29 (s, 3H), 2.15 (s, 3H), 2.07 (s, 3H), 1.98 (s, 3H), 1.57 (s, 3H).

Example 16: Synthesis of (PPh₃)₂Cl₂Ru(3-4-fluorophenyl-inden-1-ylidene) (16B)

Scheme 16: Synthesis of (PPh₃)₂Cl₂Ru(3-4-fluorophenyl-inden-1-ylidene) (16B)

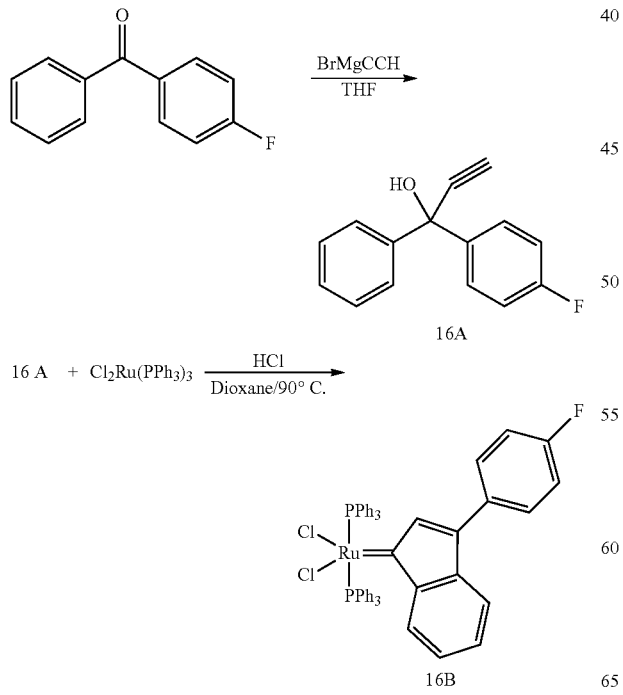

Step 1: 1-(4-fluorophenyl)-1-phenylprop-2-yn-1-ol (16A)

Ethynylmagnesium bromide (1.2 eq, 12.7 mmol, 25.4 ml) (0.5M in THF) was added to (4-fluorophenyl)(phenyl) methanone (1 eq., 10.6 mmol, 2.12 g) in dry THF (7 ml). The resulting solution was allowed to heat up under reflux overnight. The crude mixture was quenched by addition of 1N HCl (15 ml) and diluted with diethyl ether. The organic layer was separated; the aqueous layer was extracted twice with diethyl ether. The organic layers were combined dried on anhydrous MgSO₄, filtered, and concentrated under vacuum. The product obtained after column chromatography (Hexane: EtOAc 10:1) is a yellow liquid 1.94 g yield 81%.

$^1$H NMR (300 MHz, CDCl₃, TMS): δ 7.52-7.59 (m, 1H), 7.24-7.36 (m, 3H), 6.99 (t, 2H), 2.90 (s, 1H), 2.87 (s, 1H).

$^{13}$C NMR (75 MHz, CDCl₃): δ 163.98, 160.71, 144.29, 140.36, 140.32, 128.45, 128.07, 128.03, 127.92, 125.98, 115.28, 114.99, 86.23, 75.86, 73.90.

Step 2: (PPh₃)₂Cl₂Ru(3-4fluorophenyl-inden-1-ylidene) (16B)

(PPh₃)₃RuCl₂ (1 eq., 0.575 g, 0.6 mmol) and 1-(4-fluorophenyl)-1-phenylprop-2-yn-1-ol (compound 16A, 1.5 eq., 0.20 g, 0.9 mmol) were added in 4 ml HCl/dioxane solution (0.15 mol/l). The solution was heated to 90° C. for 3 hour, after which the solvent was removed under vacuum. Hexane (20 ml) was added to the flask and the solid was ultrasonically removed from the wall. The resulting suspension was filtered and washed two times using hexane (5 ml). The remaining solvent was evaporated affording a red-brown powder; 0.49 g (Yield: 90%). The product was characterized by NMR spectra $^{31}$P.

$^{31}$P NMR (121.49 MHz, CDCl₃): δ 28.26.

Example 17: Synthesis of (PCy₃)₂Cl₂Ru(3-4-fluorophenyl-inden-1-ylidene) (17)

Scheme 17: Synthesis of (PCy₃)₂Cl₂Ru(3-4-fluorophenyl-inden-1-ylidene) (17)

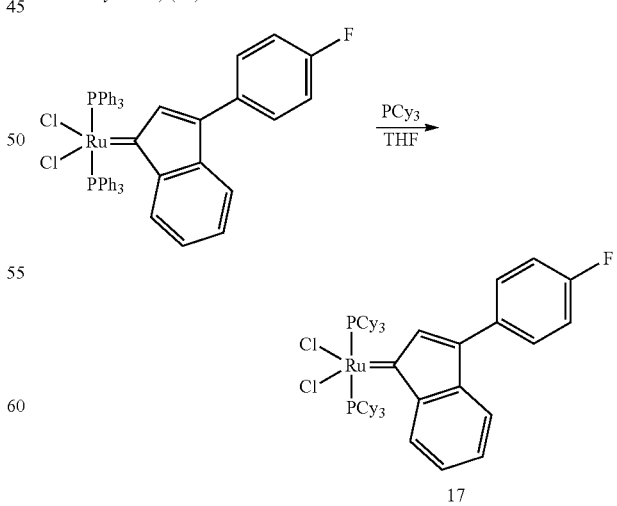

A 25 ml vial was charged with (PPh₃)₂Cl₂Ru(3-4-fluorophenyl-inden-1-ylidene) (1 eq., 0.4520 g, 0.5 mmol), tricyclohexylphosphine (3 eq., 0.42 g, 1.5 mmol) and dichloromethane (10 ml). After completion of the reaction (1 h) the resulting slurry was dried under vacuum and 20 ml isopropanol was added. Filtration afforded a red brown powder, which after washing with 5 ml isopropanol (2×) and drying under vacuum afforded 0.40 g of catalyst (Yield: 85%). The product was characterized by $^1$H and $^{31}$P NMR.

Characteristic values of $^1$H and $^{31}$P: H—C8: 8.67 ppm (d, 1H) and P: 32.33 ppm.

Example 18: Synthesis of (PPh$_3$)$_2$Cl$_2$Ru(3-i-propyl-inden-1-ylidene) (18B)

Scheme 18: Synthesis of (PPh3)2Cl2Ru(3-i-propyl-inden-1-ylidene) (18B)

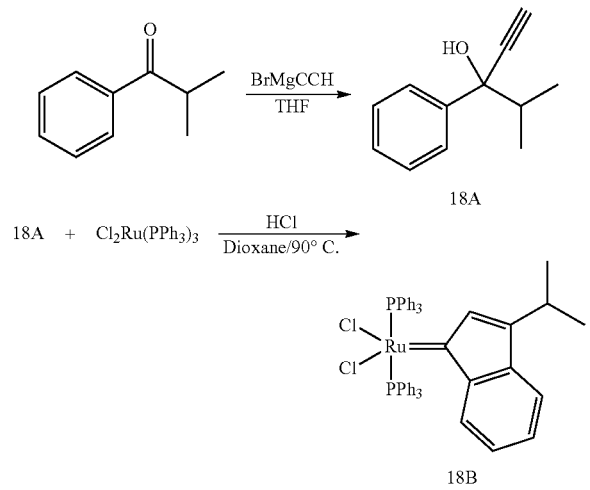

Step 1: 1-i-propyl-1-phenyl-prop-2-yn-1-ol (18A)

Ethynylmagnesium bromide (1.2 eq, 12.7 mmol, 25.4 ml) (0.5M in THF) was added to (i-propyl)(phenyl)methanone (1 eq., 10.6 mmol, 1.57 g) in dry THF (7 ml). The resulting solution was allowed to heat up under reflux overnight. The crude mixture was quenched by addition of 1N HCl (15 ml) and diluted with diethyl ether. The organic layer was separated; the aqueous layer was extracted twice with diethyl ether. The organic layers were combined dried on anhydrous MgSO4, filtered, and concentrated under vacuum. The product obtained after column chromatography (Hexane: EtOAc 20:1) is a yellow liquid 1.75 g yield 95%.

$^1$H NMR (300 MHz, CDCl$_3$): δ 7.61 (dt, 2H), 7.22-7.36 (m, 3H), 2.66 (s, 1H), 2.50 (s, 1H), 2.09 (sept, 1H), 1.06 (d, 3H), 0.81 (d, 3H).

$^{13}$C NMR (75 MHz, CDCl$_3$): δ 143.42, 127.95, 127.74, 126.14, 85.03, 77.07, 74.99, 40.16, 17.90, 17.38.

Step 2: (PPh$_3$)$_2$Cl$_2$Ru(3-i-propyl-inden-1-ylidene) (18B)

(PPh$_3$)$_3$RuCl$_2$ (1 eq., 0.575 g, 0.6 mmol) and 1-(i-propyl)-1-phenylprop-2-yn-1-ol (compound 18A, 1.5 eq., 0.144 g, 0.9 mmol) were added in 4 ml HCl/dioxane solution (0.15 mol/l). The solution was heated to 90° C. for 3 hour, after which the solvent was removed under vacuum. Hexane (20 ml) was added to the flask and the solid was ultrasonically removed from the wall. The resulting suspension was filtered and washed two times using hexane (5 ml). The remaining solvent was evaporated affording a red-brown powder; 0.48 g (Yield: 93%). The product was characterized by NMR spectra $^{31}$P.

$^{31}$P NMR (121.49 MHz, CDCl$_3$): δ 29.55.

Example 19: Synthesis of (PCy$_3$)$_2$Cl$_2$Ru(3-i-isopropyl-inden-1-ylidene) (19)

Scheme 19: Synthesis of (PCy3)2Cl2Ru(3-i-isopropyl-inden-1-ylidene) (19)

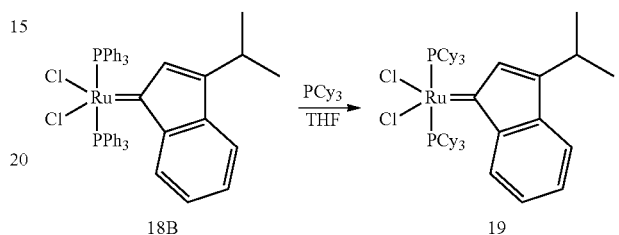

A 25 ml vial was charged with (PPh$_3$)$_2$Cl$_2$Ru(3-i-propyl-inden-1-ylidene) (1 eq., 0.4260 g, 0.5 mmol), tricyclohexylphosphine (3 eq., 0.42 g, 1.5 mmol) and dichloromethane (10 ml). After completion of the reaction (1 h) the resulting slurry was dried under vacuum and 20 ml isopropanol was added. Filtration afforded a red brown powder, which after washing with 5 ml isopropanol (2×) and drying under vacuum afforded 0.40 g of catalyst (Yield: 90%). The product was characterized by NMR spectra $^1$H and $^{31}$P.

Characteristic values of $^1$H and $^{31}$P: H—C8: 8.57 ppm (d, 1H) and P: 31.44 ppm.

Metathesis Reactions:

Representative experimental protocols for ring closing metathesis (RCM) reactions are presented in the examples below.

List of Catalysts Used in the Examples:

| Catalysts name | Catalyst Number |
| --- | --- |
| (PCy$_3$)$_2$Cl$_2$Ru(3-2-methylphenyl-5-methyl-inden-1-ylidene) | 8 |
| (PCy$_3$)$_2$Cl$_2$Ru(3-t-butyl-inden-1-ylidene) | 10 |
| (PCy$_3$)$_2$Cl$_2$Ru(3-naphtyl-inden-1-ylidene) | 11 |
| (PCy$_3$)$_2$Cl$_2$Ru(3-c-hexyl-inden-1-ylidene) | 12 |
| (PCy$_3$)$_2$Cl$_2$Ru(3-2,6-dimethylphenyl-inden-1-ylidene) | 13 |
| (PCy$_3$)$_2$Cl$_2$Ru(3-4-florophenyl-inden-1-ylidene) | 17 |
| (PCy$_3$)$_2$Cl$_2$Ru(3-i-isopropyl-inden-1-ylidene) | 19 |
| (PCy$_3$)$_2$Cl$_2$Ru(3-phenyl-inden-1-ylidene) | F |

List of Substrates Used in the Examples:

| Substrate name | Symbol |
| --- | --- |
| diethyl 2,2-diallylmalonate | DE |
| diethyl 2-allyl-2-(2-methylallyl)malonate | DE1 |
| diethyl 2-allyl-2-(but-3-en-1-yl)malonate | DE4 |
| diethyl 2-allyl-2-(pent-4-en-1-yl)malonate | DE5 |
| N-allyl-4-methyl-N-vinylbenzenesulfonamide | DA |
| N-allyl-4-methyl-N-(2-methylallyl)benzenesulfonamide | DA1 |
| N-allyl-N-(but-3-en-1-yl)-4-methylbenzenesulfonamide | DA4 |
| N-allyl-4-methyl-N-(pent-4-en-1-yl)benzenesulfonamide | DA5 |

Example 20: Effect of Catalyst Loading, Comparison Commercial Available Fürstner Catalyst (F) with Newly Developed Catalyst 8

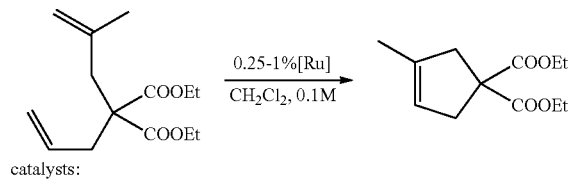

catalysts:

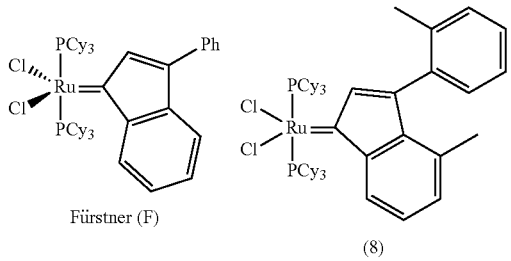

Fürstner (F)                    (8)

RCM of DE1 was used to determine the activity of catalyst 8 and catalyst F with different catalyst loadings (1%, 0.5% and 0.25).

A substrate stock solution of DE1 was made by dissolving DE1 (2.54 g, 10 mmol) and dodecane as internal standard (1.7 g, 10 mmol) in 50 ml anhydrous dichloromethane to obtain a substrate concentration of 0.2 mmol/ml.

Catalyst stock solutions were made by dissolving catalyst 8 (0.038 g, 0.04 mmol) and catalyst F (0.037 g, 0.04 mmol) in anhydrous dichloromethane 20 ml respectively, obtaining a catalyst concentration of 0.002 mmol/ml.

For experiments with 1% catalyst loading: 5 ml DE1 stock solution and 5 ml catalyst stock solution were transferred in a Schlenk flask and thereafter placed in an oil bath at 38° C.

For experiments with 0.5% catalyst loading: 5 ml DE1 stock solution, 2.5 ml catalyst stock solution and 2.5 ml anhydrous dichloromethane were transferred in a Schlenk flask and thereafter placed in an oil bath at 38° C.

For experiments with 0.25% catalyst loading: 5 ml DE1 stock solution, 1.25 ml catalyst stock solution and 3.75 ml anhydrous dichloromethane were transferred in a Schlenk flask and thereafter placed in an oil bath at 38° C.

0.1 ml of the reaction mixture was taken as sample for analysis with GC (0.1 ml sample was dissolved in 0.4 ml dichloromethane and from this solution the required amount was taken to inject into the gas chromatograph.

Figure 3:
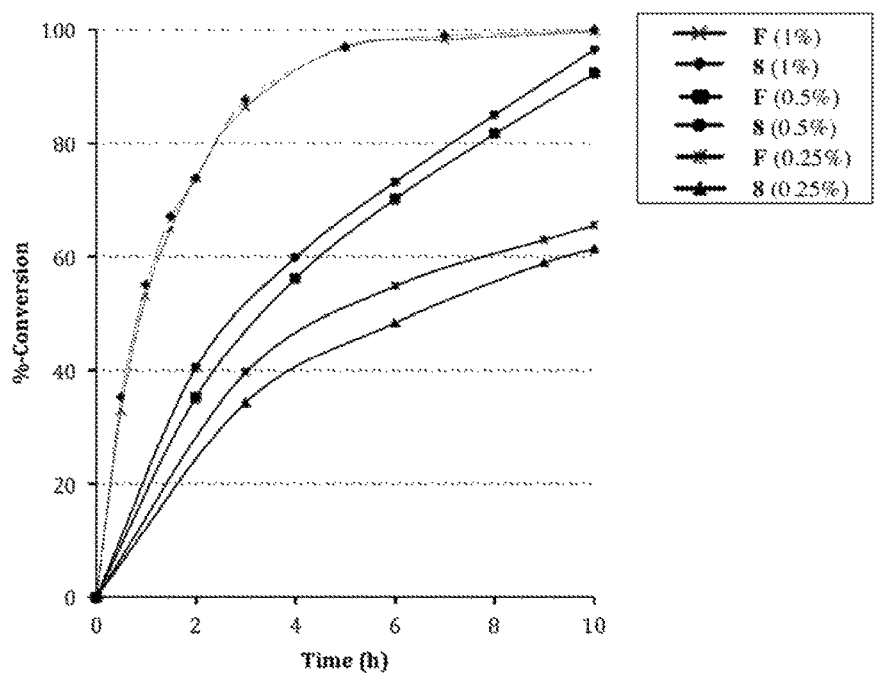
FIG. 3 is RCM diethyl 2-allyl-2-(2-methylallyl)malonate using catalyst F and 8 (0.25-1 mol %) in $CH_2Cl_2$ at 38° C.

The results are depicted in FIG. 3.

Example 21: Comparison of Different Catalysts for RCM of DE1

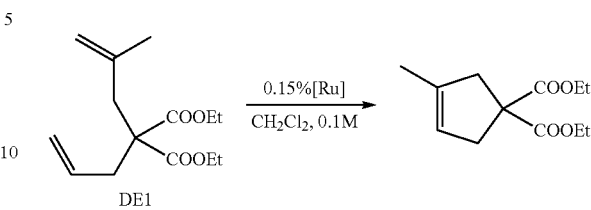

DE1

A substrate stock solution of DE1 was made by dissolving DE1 (2.54 g, 10 mmol) and dodecane, as internal standard, (1.77 g, 10 mmol) in 100 ml anhydrous dichloromethane to obtain a DE1 concentration of 0.1 mmol/ml.

Experiments were performed using 0.15% catalyst loading. 15 ml DE1 stock solution and the required amount of catalyst were transferred in a Schlenk flask and placed in an oil bath at 40° C. [catalyst 8: 1.43 mg, 1.5 mmol; catalyst 17: 1.41 mg, 1.5 mmol; catalyst 11: 1.46 mg, 1.5 mmol; catalyst F: 1.38 mg, 1.5 mmol; catalyst 13: 1.43 mg, 1.5 mmol)].

0.1 ml of the reaction mixture was taken as sample for analysis with GC (0.1 ml sample was dissolved in 0.4 ml dichloromethane and from this solution the required amount was taken to inject into the gas chromatograph).

Figure 4:
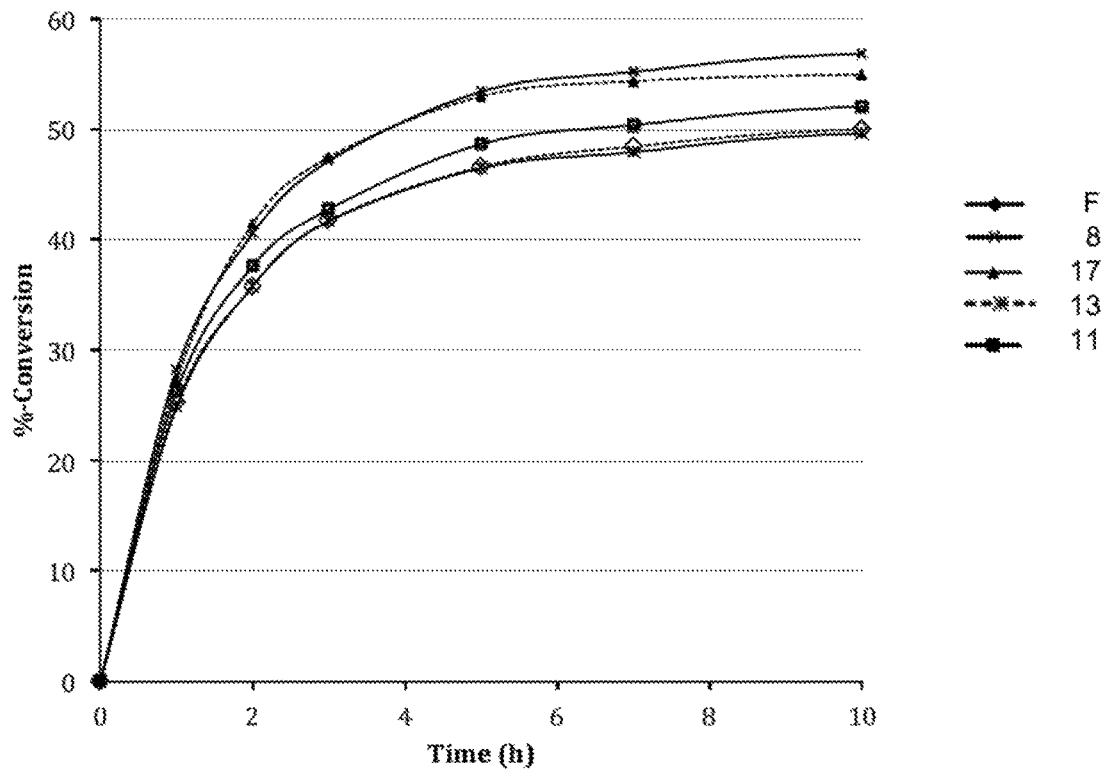
FIG. 4 is RCM of diethyl 2-allyl-2-(2-methylallyl)malonate using 0.15 mol % catalysts F, 8, 11, 13 and 17.

The results are depicted in FIG. 4.

Example 22: RCM of Different Substrates Using Different Catalyst

Different substrate stock solutions with a concentration of 0.1 mmol/ml were prepared by transferring 10 mmol substrate and dodecane, as internal standard, (1.7 g, 10 mmol) in 100 ml anhydrous dichloromethane. [substrate DE: 2.4 g; substrate DE4: 2.54 g; substrate DE5: 2.5468 g; substrate DA: 2.51 g; substrate DA1: 2.65 g; substrate DA4: 2.65 g; substrate DA5: 2.79 g]. Experiments were performed using 0.25% catalyst loading. 10 ml substrate solution and the required amount of catalyst (2.5 mmol) were transferred in a Schlenk flask and placed in an oil bath at 40° C. [catalyst 8: 2.38 mg; catalyst 17: 2.35 mg; catalyst 11: 2.43 mg; catalyst 13: 2.38 mg; catalyst 10: 2.26 mg; catalyst 12: 2.32 mg; catalyst 19: 2.22 mg]

0.1 ml of the reaction mixture was taken as sample for analysis with GC (0.1 ml sample was dissolved in 0.4 ml dichloromethane and from this solution the required amount was taken to inject into the gas chromatograph).

| Substrate | Catalyst loading (mol %) | Temp (° C.) | Time (h) | Catalyst 8 | 17 | 11 | 13 | 10 | 12 | 19 |
|---|---|---|---|---|---|---|---|---|---|---|
| DE | 0.25 | 30 | 5 | 99 | 99 | 99 | 99 | 99 | 99 | 99 |
| DE1 | 0.15 | 40 | 10 | 57 | 55 | 52 | 50 | 92 | 88 | 88 |
| DE4 | 0.25 | 30 | 0.75 | 98 | 97 | 84 | 82 | 95 | 92 | 94 |
| DE5 | 0.25 | 35 | 2.75 | 99 | 99 | 98 | 95 | 96 | 98 | 95 |
| DA | 0.25 | 30 | 1 | 98 | 98 | 96 | 96 | 97 | 96 | 97 |
| DA1 | 0.25 | 35 | 3 | 52 | 46 | 39 | 35 | 50 | 51 | 56 |
| DA4 | 0.25 | 30 | 0.25 | >99 | >99 | >99 | >99 | >99 | >99 | >99 |
| DA5 | 0.25 | 30 | 1 | >99 | 99 | 99 | 99 | 99 | 99 | 99 |

Example 23: Monitoring Ring Opening Metathesis Polymerization (ROMP) of Cyclo-Octadiene (COD)

After charging an NMR tube with the appropriate amount of catalyst dissolved in deuterated solvent (CDCl$_3$), COD was added. The polymerization reaction was monitored as a function of time at 20° C. by integrating olefinic $^1$H-signals of the formed polymer (5.38-4.44 ppm) and the consumed monomer (5.58 ppm).

catalyst/COD: 1/300, catalyst concentration: 0.452 mM.

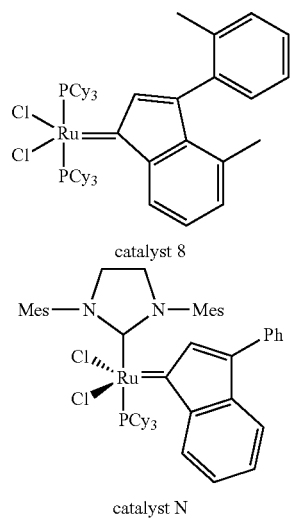

catalyst 8

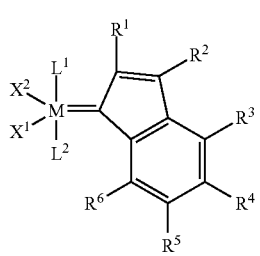

catalyst N

Figure 5:
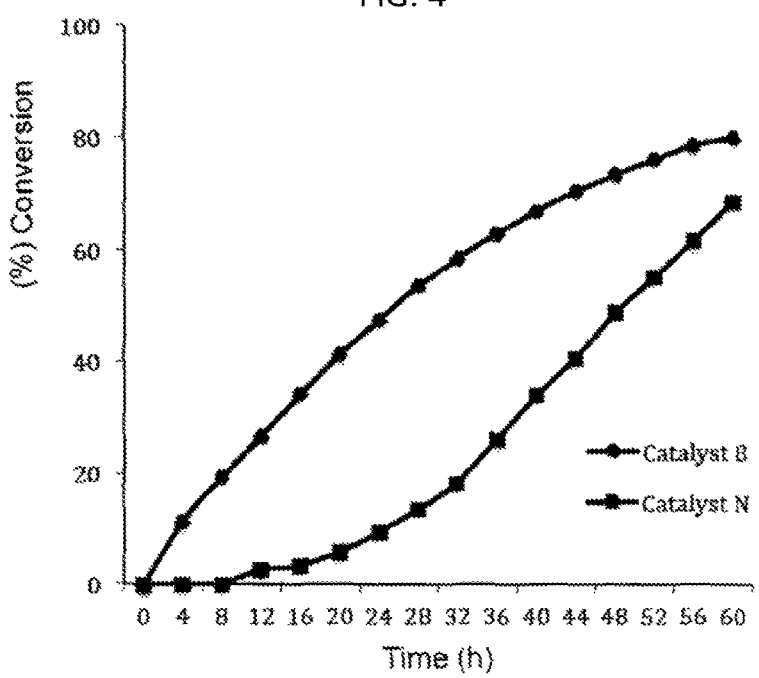
FIG. 5 is ROMP of cyclo-octadiene using catalysts $(PCy_3)_2Cl_2Ru(3\text{-}2\text{-methylphenyl-5-methylinden-1-ylidene}$ (8) and $(PCy_3)(SIMes)Cl_2Ru(phenylinden\text{-}1\text{-ylidene}$ (N).

The results are depicted in FIG. 5.

The invention claimed is:

1. A catalyst with a carbene ligand having a general structure of formula (I):

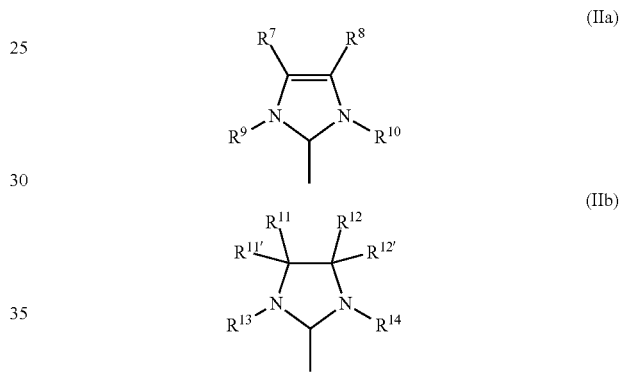

wherein
M is a Group 8 transition metal;
X$^1$ and X$^2$ are identical or different and represent halogen;
R$^1$, R$^4$-R$^6$ are identical and represent hydrogen;
R$^2$ represents 2-methylphenyl, t-butyl, naphtyl, c-hexyl, 2,6-dimethylphenyl, 4-fluorophenyl, or i-propyl;
R$^3$ represents methyl, methoxy or hydrogen; and
L$^1$ and L$^2$ are identical or different ligands, and represent neutral electron donors.

2. The catalyst of claim 1, wherein M is Ru or Os.

3. The catalyst of claim 1, wherein L$^1$ and L$^2$ are independently selected from phosphine, sulphonated phosphine, phosphate, phosphinite, phosphonite, phosphite, ether, amine, amide, pyridine, substituted pyridine, pyrazine, thio-ether, N-heterocyclic carbene (NHC), substituted NHC, or a cyclic alkyl amino carbene (CAAC).

4. The catalyst of claim 1, wherein one of the two ligands L$^1$ and L$^2$ independently of one another represents a phosphine ligand having the formula P(L$^3$)$_3$ with L$^3$ are identical or different and are C$_1$-C$_5$-alkyl, cyclopentyl, cyclohexyl, neopentyl, phenyl or toluyl, C$_1$-C$_{10}$ alkyl-phosphabicyclononane, C$_3$-C$_{20}$ cycloalkyl phospha-bicyclononane, or a sulfonated phosphine ligand of formula P(L$^4$)$_3$ wherein L$^4$ represents a mono- or poly-sulfonated L$^3$-ligand.

5. The catalyst of claim 1, wherein one of the two ligands L$^1$ or L$^2$ represents a pyridine ligand selected from pyridine, picolines (α-, β-, and γ-picoline), lutidines (2,3-, 2,4-, 2,5-, 2,6-, 3,4- and 3,5-lutidine), collidine (2,4,6-trimethylpyridine), trifluoromethylpyridine, phenylpyridine, 4-(dimethylamino) pyridine, chloropyridines (2-, 3- and 4-chloropyridine), bromopyridines (2-, 3- and 4-bromopyridine), nitropyridines (2-, 3- and 4-nitropyridine), quinoline, pyrimidine, pyrrole, imidazole and phenylimidazole.

6. The catalyst of claim 1, wherein one of the two ligands L$^1$ and L$^2$ represents a N-heterocyclic carbene (NHC) having a general structure of the formulas (IIa) or (IIb),

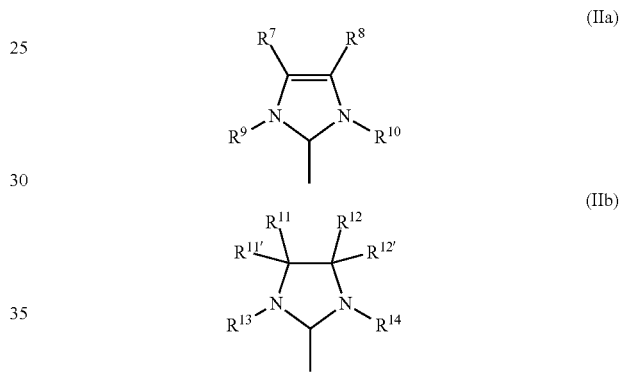

wherein
R$^7$-R$^{14}$, R$^{11'}$, R$^{12'}$ are identical or different and are hydrogen, straight or branched C$_1$-C$_{30}$ alkyl, C$_3$-C$_{20}$ cycloalkyl, C$_2$-C$_{20}$ alkenyl, C$_2$-C$_{20}$ alkynyl, C$_6$-C$_{24}$ aryl, C$_1$-C$_{20}$ carboxylate, C$_1$-C$_{20}$ alkoxy, C$_2$-C$_{20}$ alkenyloxy, C$_2$-C$_{20}$, alkynyloxy, C$_6$-C$_{20}$ aryloxy, C$_2$-C$_{20}$ alkoxycarbonyl, C$_1$-C$_{20}$ alkylthio, C$_6$-C$_{20}$ arylthio, C$_1$-C$_{20}$ alkylsulfonyl, C$_1$-C$_{20}$ alkyl sulfonate, C$_6$-C$_{20}$ aryl sulfonate or C$_1$-C$_{20}$ alkyl sulfinyl.

7. The catalyst of claim 1, wherein one of the two ligands L$^1$ or L$^2$ represents a cyclic alkyl amino carbenes (CAACs) having a general structure of the Formula (IV):

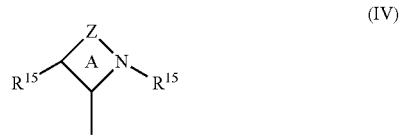

wherein the ring A is a 4-, 5-, 6-, or 7-membered ring, and Z is a linking group comprising from one to four linked vertex atoms selected from the group consisting of C, O, N, P, S and Si with available valences optionally occupied by hydrogen, oxo or R-substituents, wherein R is independently selected from the group consisting of C$_1$ to C$_{12}$ hydrocarbyl groups, substituted C$_1$ to C$_{12}$ hydrocarbyl groups, and halides, and each R$^{15}$ is independently a hydrocarbyl group or substituted hydrocarbyl group selected from methyl, ethyl, propyl, butyl including isobutyl and n-butyl, pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluyl, chlorophenyl, phenol, or substituted phenol.

8. A method for synthesizing catalyst with carbene ligand according to claim 1, comprising contacting a precursor compound of the formula $(X^1X^2ML_3)$ or $(X^1X^2ML_4)$ with an acetylenic compound, optionally comprising a chelating moiety,
wherein for the precursor compound, each of $L_3$ and $L_4$ represents neutral electron donor ligands.

9. The method of claim 8, wherein the acetylenic compound contains a chelating moiety having the general formula (VI)

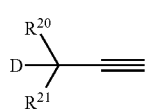

(VI)

wherein,
D is a leaving group;
$R^{20}$ to $R^{21}$ are as defined below, and may contain $R^{16}$-$Q^1$-$Q^2$;
$R^{20}$ is selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, and wherein when $R^{20}$ is aryl, polyaryl, or heteroaryl, $R^{20}$ is substitutable with any combination of $R^1$, $R^2$, $R^3$, $R^4$, $R^5$, and $R^6$ and is linkable with any of $R^1$, $R^2$, $R^3$, $R^4$, $R^5$, and $R^6$ to form one or more cyclic aromatic or non-aromatic groups;
$R^{21}$ is selected from annulenes, having the general formula $C_nH_n$ when n is an even number or $C_nH_{n+1}$ when n is an odd number, wherein annulenes are cyclobutadiene, benzene, and cyclooctatetraene, wherein annulenes are aromatic or anti-aromatic, every H-atom from the annulene fragment is substitutable by halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, amino sulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, and wherein when $R^{21}$ is aryl, polyaryl, or heteroaryl, $R^{21}$ is substitutable with any combination of R1, $R^2$, $R^3$, $R^4$, $R^5$, and is linkable with any of $R^1$, $R^2$, $R^3$, $R^4$, $R^5$ and $R^6$ to form one or more cyclic aromatic or non-aromatic groups.

10. The method of claim 8, wherein the acetylenic compounds are of the formula (VII),

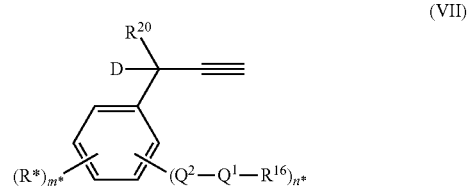

(VII)

wherein
n* is an integer from 0 to 5;
m* is an integer from 1 to 5; and m*=5−n*; and
R* is selected from $R^1$, $R^2$, $R^3$, $R^4$, $R^5$ and $R^6$, or combinations thereof.

11. The method of claim 8, further comprising:
mixing the precursor compound of the formula $(X^1X^2ML_3)$ or $(X^1X^2ML_4)$ with an acetylenic compound in solution of acid/polar solvent;
heating the solution from 40° C. to 200° C., wherein the solution is heated less than 10 hours;
removing the polar solvent and adding a non-polar solvent; filtering and washing the resulting suspension using the same non-polar solvent;
wherein the molar ratio of the precursor compound to acetylenic compound is 1-20.

12. The catalyst of claim 1, wherein $X^1$ and $X^2$ are identical and are chlorine.

13. A catalyst with a carbene ligand having a general structure of formula (I):

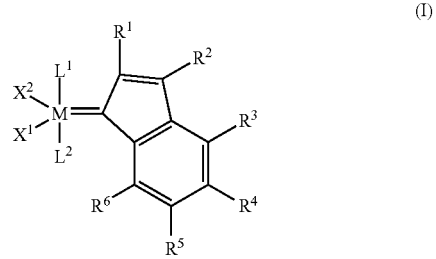

(I)

wherein
M is a Group 8 transition metal;
$X^1$ and $X^2$ are identical or different and represent halogen;
$R^1$, $R^4$-$R^6$ are identical and represent hydrogen;
$R^2$ represents 2-methylphenyl, 2-methoxyphenyl, t-butyl, naphtyl, c-hexyl, 2,6-dimethylphenyl, 4-fluorophenyl, or i-propyl;
$R^3$ represents methyl or methoxy; and
$L^1$ and $L^2$ are identical or different ligands, and represent neutral electron donors.

* * * * *